US008021672B2

(12) United States Patent
O'Connell

(10) Patent No.: US 8,021,672 B2
(45) Date of Patent: Sep. 20, 2011

(54) **DEVELOPMENT OF A *CHLAMYDIA* SP. VACCINE STRAIN**

(75) Inventor: Catherine M. O'Connell, Little Rock, AR (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 762 days.

(21) Appl. No.: 11/708,620

(22) Filed: Feb. 20, 2007

(65) Prior Publication Data
US 2007/0196392 A1    Aug. 23, 2007

Related U.S. Application Data

(60) Provisional application No. 60/776,070, filed on Feb. 23, 2006.

(51) Int. Cl.
*A61K 39/118* (2006.01)

(52) U.S. Cl. ..................................... 424/263.1; 435/243

(58) Field of Classification Search ........................ None
See application file for complete search history.

(56) References Cited

OTHER PUBLICATIONS

J.T. Trevors (FEMS Microbio. 1986. 32(3-4): 149-157).*
Banks, J., Eddie, B., Schachter J & Meyer, K. F. (1970). Plaque formation by *Chlamydia* in L cells. Infect Immun 1, 259-262.
Brunham, R. C. & Rey-Ladino, J. (2005) Nat. Rev. Immunol 5, 149-161.
Chin, S.C., Abdullah, N. Siang, T.W. & Wan, H.Y. (2005). Plasmid profiling and curing of *Lactobacillus* strains isolated from the gastrointestinal tract of chicken. J. Microbiol. 43, 251-256.
Darville, T., Andrews, C. W., Jr., Laffoon, K. K., Shymasani, W., Kishen, L. R. & Rank, R. G. (1997) Infect. Immun. 65, 3065-3073.
Darville T, O'Neill JM, Andrews CW Jr, Nagarajan UM, Stahl L, Ojcius DM. (2003). Toll-like receptor-2, but not Toll-like receptor-4, is essential for development of oviduct pathology in Chlamydial genital tract infection. J Immunol. 171(11), 6187-97.
Farencena, A., Comanducci, M., Donati, M., Ratti, G. & Cevenini, R. (1997). Characterization of a new isolate of *Chlamydia trachomatis* which lacks the common plasmid and has properties of biovar trachoma. Infect Immun 65, 2965-2969.
Grayston JT, Wang SP, Kuo CC, Campbell LA. (1989) Current knowledge on *Chlamydia pneumoniae*, strain TWAR, an important cause of pneumonia and other acute respiratory diseases. Eur J Clin Microbiol Infect Dis. 8(3), 191-202.
Hooper, D. C., Wolfson, J. S., McHugh, G. L., Swartz, M. D., Tung, C. & Swartz, M. N. (1984). Elimination of plasmid pMG110 from *Escherichia coli* by novobiocin and other inhibitors of DNA gyrase. Antimicrob Agents Chemother 25, 586-590.
Kelly, K.A., Robinson, E.A., & Rank, R.G. (1996). Initial route of antigen administration alters the T-cell cytokine profile produced in response to the mouse pneumonitis biovar of *Chlamydia trachomatis* following genital infection. Infect Immun 64:4976-83.
Matsumoto, Akira, et al., Plaque Formation by and Plaque Cloning of *Chlamydia trachomatis* Biovar Trachoma, Journal of Clinical Microbiology, vol. 36, No. 10, Oct. 1998, pp. 3013-3019.
Miyashita, N., Matsumoto, A. & Matsushima, T. (2000). In vitro susceptibility of 7.5-kb common plasmid-free *Chlamydia trachomatis* strains. Microbiol Immunol 44, 267-269.
O'Connell, C. M., lonova, I. A., Quayle, A. J., Visintin, A. & Ingalls, R. R. (2006) J. Biol. Chem. 281, 1652-1659.
O'Connell, Catherine M., et al., A plasmid-cured *Chlamydia muridarum* strain displays altered plaque morphology and reduced infectivity in cell culture, Microbiology, vol. 152, Jun. 2006, pp. 1601-1607.
Pal, S., Peterson, E. M., Rappuoli, R., Ratti, G., & De La Maza, L. M. (2006) Vaccine 24, 766-775.
Perez-Martinez JA, Storz J. (1985). Antigenic diversity of *Chlamydia psittaci* of mammalian origin determined by microimmunofluorescence. Infect Immun. 50(3), 905-10.
Peterson, E. M., Markoff, B. A., Schachter, J. & De La Maza, L. M. (1990). The 7.5-kb plasmid present in *Chlamydia trachomatis* is not essential for the growth of this microorganism. Plasmid 23, 144-148.
Pickett, Mark A., et al. The plasmids of *Chlamydia trachomatis* and *Chlamydophila pneumoniae* (N16): accurate determinatin of copy number and the paradoxical effect of plasmid-curing agents, Microbiology, vol. 151, 2005, pp. 893-903.
Sabet SF, Simmons J, Caldwell HD. (1984). Enhancement of *Chlamydia trachomatis* infectious progeny by cultivation of HeLa 229 cells treated with DEAE-dextran and cycloheximide. J. Clin Micbrobiol 20(2), 217-222.
Spengler, Gabriella, et al., Enhancement of plasmid curing by 9-aminoacridine and two phenothiazines in the presence of proton pump inhibitor 1-(2-benzoxazolyl)-3,3,3-trifluoro-2-propanone, International Journal of Antimicrobial Agents, vol. 22, No. 3, Sep. 2003, pp. 223-227.
Spengler, Gabriella, et al., The Mechanism of Plasmid Curing in Bacteria, Current Drug Targets, vol. 7, No. 7, Jul. 2006, pp. 823-841 (Abstract).
Stephens, R. S., Kalman, S., Lammel, C. & other authors (1998). Genome sequence of an obligate intracellular pathogen of humans: *Chlamydia trachomatis*. Science 282, 754-759.
Stothard, D. R., Williams, J. A., Van Der, P. B. & Jones, R. B. (1998). Identification of a *Chlamydia trachomatis* serovar E urogenital isolate which lacks the cryptic plasmid. Infect Immun 66, 6010-6013.
Tropp, B. E., Ragolia, L., Xia, W., Dowhan, W., Milkman, R., Rudd, K. E., Ivanisevic, R. & Savic, D. J. (1995). Identity of the *Escherichia coli* cls and nov genes. J Bacteriol 177, 5155-5157.
Wolfson, John S. et al., Novobiocin-Induced elimination of F'lac and Mini-F Plasmids from *Escherichia coli*, Journal of Bacteriology, vol. 156, No. 3, Dec. 1983, pp. 1165-1170.

* cited by examiner

*Primary Examiner* — Jennifer Graser
(74) *Attorney, Agent, or Firm* — Hugh McTavish

(57) ABSTRACT

The invention involves the discovery that *Chlamydia* sp. strains can be cured of their plasmids by treatment with novobiocin, and that plasmid-deficient strains are defective in infecting cells under standard conditions, but can infect cells if centrifuged onto the host cells. But it is found that plasmid-deficient strains with wild-type infection efficiency under standard conditions can be isolated as mutants from parent plasmid-deficient strains with low infectivity by selecting for infection under standard conditions. Both the less infective and the highly infective plasmid-deficient strains were able to infect mice with little or no pathological symptoms, and both reduced the pathology in mice later challenged with the parental wild-type disease-causing *Chlamydia* strain. Thus, plasmid-deficient *Chlamydia* are effective vaccine strains. The invention provides a process for isolating a plasmid-deficient strain of *Chlamydia* sp., a process for developing a plasmid-deficient strain of *Chlamydia* sp. for use as a vaccine, a process for developing a highly infective plasmid-deficient strain of *Chlamydia* sp., isolated *Chlamydia* sp. strains, a method of expressing a recombinant nucleic acid in *Chlamydia* sp., and a method of immunizing a mammal against a *Chlamydia* infection.

4 Claims, 10 Drawing Sheets

DEVELOPMENT OF A *CHLAMYDIA* SP. VACCINE STRAIN

This application claims priority from U.S. provisional patent application Ser. No. 60/776,070, filed Feb. 23, 2006.

BACKGROUND

Chlamydiae are obligate intracellular Gram negative bacteria which replicate only in cytoplasmic inclusions of eukaryotic cells. They have a unique developmental cycle that is represented by two major forms, the spore-like elementary body (EB) infectious form, which is transmitted from cell to cell, and the non-infectious, metabolically active reticulate body (RB) which replicates within the host-cell.

The genus *Chlamydia* contains at least five species of obligate parasitic bacteria: *Chlamydia psittaci, C. pecorum, C. pneumoniae, C. muridarum*, and *C. trachomatis*. This unique genus causes a variety of diseases in humans, mammals, and birds. *Chlamydia trachomatis* and *C. pneumoniae* are important human pathogens. The recently defined species *C. pneumoniae* (Grayston 1989) is now recognized as a major cause of respiratory tract infections (Grayston 1993) and data are now growing for an association with atherosclerosis. The association is supported by seroepidemiological studies, studies demonstrating the presence of the bacterium in the atherosclerotic lesions, studies showing *C. pneumoniae* capability to replicate in the different cell types present in the atherosclerotic lesions, interventional trials with antibiotics in patients with coronary artery disease and experimental respiratory tract infection in rabbits or apolipoprotein-E deficient mice which leads to inflammatory changes in the aorta (Danesh 1997, Fong 1997, Laitinen 1997). Overall, those data implicate *C. pneumoniae* as a causative and/or aggravating factor of atherosclerosis.

*C. trachomatis* is a major human pathogen that is transmitted from human to human (there is no known animal reservoir). It causes ocular and genital infections that can result in long term sequelae. Trachoma, a Chlamydial ocular infection, is endemic in several developing countries and is the leading cause of preventable blindness worldwide with millions of people affected by the disease. Genital Chlamydial infections constitute the most common bacterial sexually transmitted disease (STD). In 1996, WHO generated a new set of global estimates for four major STDs drawing an extensive review of the published and unpublished prevalence data (Gerbase 1998). It has been estimated that in 1995, 4 and 5.2 million new cases of *C. trachomatis* infection occurred in individuals aged 15-49 for North America and Western Europe, respectively. Data show higher infection rates in women as compared to men. Higher incidence is also found in adolescents and young adults—approximately 70% of the Chlamydial infections being reported in the 15-24 year age group. There is a clear need for effective vaccines against *Chlamydia trachomatis* and *C. pneumoniae*.

*C. psittaci* causes psitacosis in humans, and in animals, *C. psittaci* can cause a diverse range of disease in livestock, poultry, turkeys and companion birds. The known *C. psittaci* strains have been grouped into eight biovars (Perez-Martinez, J A and J Storz, 1985). Strains of serovar 1 are mainly associated with intestinal infections and abortions, while strains of serovar 2 cause polyarthritis, encephalitis, and conjunctivitis in ruminants. Avian strains of *C. psittaci* cause respiratory problems and diarrhea in birds (Storz, 1988). The organism can also be transmitted to humans from these animals, and outbreaks have been documented in animal production workers. Thus, there is a need for an effective vaccine against *C. psittaci* for mammalian and avian species.

A highly conserved plasmid of approximately 7.5 kb, is present in almost all strains of *C. trachomatis* with copy numbers estimated to range from 4 (Pickett et al., 2005) to 10 (Tam et al., 1992) copies per cell. The role of this plasmid is unknown. However, at least one of the plasmid-encoded ORFs is expressed during infection (Comanducci et al., 1993). Naturally occurring plasmid-deficient clinical isolates are extremely rare; only three strains have been described (Peterson et al., 1990; Farencena et al., 1997; Stothard et al., 1998). In contrast, Matsumoto et al. described the isolation and characterization of three plasmid-deficient *C. trachomatis* strains that occur naturally in tissue-culture propagated cultures at an estimated rate of 1% (Matsumoto et al., 1998). The derivatives identified by Matsumoto et al. appeared unable to accumulate glycogen within the intracytoplasmic inclusions that are formed by the bacteria as they grow. No other phenotypic changes were detected that could be attributed to the presence of the plasmid (Miyashita et al., 2000).

Currently, a genetic system for use in Chlamydiae is lacking. A better understanding of the mechanisms by which the conserved plasmid, a potential gene delivery vector, is maintained, and the ability to generate at high efficiency plasmid-deficient derivatives of the most highly characterized Chlamydiae for use as recipient strains would advance progress in this area.

SUMMARY

The majority of *Chlamydia* sp. carry a conserved plasmid, which in the case of *C. trachomatis* is about 7.5 kb. The invention involves curing chlamydiae of this plasmid, which was achieved by treatment with slightly sublethal doses of the antibiotic novobiocin. Plasmid-free *C. muridarum* were found to not accumulate glycogen within intracytoplasmic inclusions as wild-type *C. muridarum* and *C. trachomatis* do, and to be defective in infecting host cells under standard conditions. However, with centrifugation onto host cells, the plasmid-free strain was able to infect host cells with close to the same efficiency as wild-type. The plasmid-free strain *C. muridarum* CM972, and almost all the other plasmid-free strains initially observed also produced smaller plaques than the wild type *C. muridarum* Nigg.

Incubation of host cells with a high multiplicity of infection of *C. muridarum* CM972 without centrifugation resulted in the identification of a plasmid-free derivative strain that was able to infect host cells in vitro without centrifugation at approximately the same efficiency as wild-type *C. muridarum* Nigg. This highly infective plasmid-free derivative strain was designated *C. muridarum* CM3.1. *C. muridarum* CM3.1 also produced larger infective plaques than strain CM972. Like the other plasmid-free strains, it did not accumulate glycogen within its inclusions. However, *C. muridarum* CM3.1 was able to infect cells in mice with the same efficiency as the wild type. It also appeared to induce an immune response, as shown by host clearance of *C. muridarum* CM3.1 at a similar rate to clearance wild type *C. muridarum* Nigg. But *C. muridarum* CM3.1 caused little inflammation and little or no reproductive tract pathology in the mouse, unlike *C. muridarum* Nigg.

Both *C. muridarum* CM3.1 and CM972 are able to infect mice and induce an immune response that clears the chlamydiae from the mice. Mice previously inoculated with either CM3.1 or CM972 were found to have greatly decreased pathology when later infected with *C. muridarum* Nigg, as compared to mice not previously exposed to CM3.1 or CM972. Thus, both CM3.1 and CM972 are effective vaccine strains. Other plasmid-deficient strains can also be effective vaccine strains for disease-causing *Chlamydia* sp.

Thus, it has been discovered that plasmid-cured wild type *Chlamydia* strains have a decreased ability to infect cells, but this can be overcome by centrifuging the bacteria onto host cells. Highly infective plasmid-deficient strains can be isolated by selecting for derivatives of plasmid-cured *Chlamydia* that are able to infect host cells at a higher efficiency without centrifugation.

The invention also provides a genetic system for genetically modifying *Chlamydia*. Plasmid-deficient strains of *Chlamydia* can be transformed with a *Chlamydia* plasmid, optionally containing engineered or recombinant nucleic acid, and transformants can be selected for by their regaining the ability to infect host cells at high efficiency without centrifugation.

One embodiment of the invention provides a process for isolating a plasmid-deficient strain of *Chlamydia* sp. comprising: (a) treating a plasmid-containing *Chlamydia* sp. strain under conditions that cure it of the plasmid to generate a population of treated *Chlamydia*; (b) incubating host cells with the treated *Chlamydia* under conditions permissive for infection by plasmid-deficient *Chlamydia* (e.g., with centrifuging the treated *Chlamydia* into host cells) to infect the host cells; (c) culturing the *Chlamydia* in the host cells and isolating plaques of *Chlamydia* from the host cells; and (d) verifying that *Chlamydia* from the isolated plaques are plasmid-deficient.

Another embodiment of the invention provides an isolated plasmid-deficient strain of *Chlamydia* sp. isolated by the process described in the previous paragraph.

Another embodiment of the invention provides a process for identifying a strain of *Chlamydia* sp. suitable for use as a vaccine involving: (a) obtaining one or more plasmid-deficient *Chlamydia* sp. strains; (b) inoculating a vertebrate (e.g., a mammal or bird) with the one or more plasmid-deficient *Chlamydia* strains; and (c) characterizing any pathologic sequelae the strains cause in the vertebrate and any immune response they cause to identify a strain suitable as a vaccine.

Another embodiment of the invention is a *Chlamydia* sp. strain suitable as a vaccine developed by the process described in the previous paragraph.

Another embodiment of the invention provides a method of expressing a recombinant nucleic acid in *Chlamydia* comprising: (a) obtaining a plasmid-deficient *Chlamydia* sp. strain; (b) contacting the plasmid-deficient *Chlamydia* with a plasmid of *Chlamydia* origin comprising a recombinant nucleic acid to generate a pool of potentially transformed *Chlamydia* cells; and (c) isolating transformed *Chlamydia* carrying the plasmid comprising the recombinant nucleic acid. Preferably the step of isolating transformed *Chlamydia* comprises incubating host cells with the pool of potentially transformed *Chlamydia* cells under conditions that are non-permissive for infection by the plasmid-deficient *Chlamydia* sp. strain and selecting for *Chlamydia* that infect the host cells.

Another embodiment of the invention provides an isolated plasmid-deficient *Chlamydia* sp. strain wherein the strain causes reduced pathology as compared to a corresponding plasmid-containing disease-causing *Chlamydia* strain in a vertebrate (e.g., a mammal or bird); and wherein following inoculation with the plasmid-deficient *Chlamydia* strain, when a vertebrate is infected with the corresponding plasmid-containing disease-causing strain the vertebrate experiences reduced pathology as compared to a mammal not previously inoculated with the one or more identified plasmid-deficient *Chlamydia* strains.

Another embodiment of the invention provides an isolated *Chlamydia muridarum* strain CM972.

Another embodiment of the invention provides an isolated *Chlamydia muridarum* strain CM3.1.

Another embodiment of the invention provides a process for developing a highly infective plasmid-deficient strain of *Chlamydia* sp. involving: (a) obtaining one or more parent plasmid-deficient *Chlamydia* sp. strains, wherein the parent plasmid free strains are less infective than a corresponding plasmid-containing strain; and (b) incubating host cells with the one or more parent plasmid-deficient *Chlamydia* sp. strains to infect the host cells and selecting for highly infective *Chlamydia* sp. variants or allowing plaques to form and harvesting one or more plaques larger than typical plaques formed by the one or more parent plasmid-deficient *Chlamydia* strains to isolate one or more highly infective plasmid-deficient *Chlamydia* sp. strains.

Another embodiment provides a method of immunizing a vertebrate (e.g., a mammal or bird) against a disease-causing *Chlamydia* infection involving: inoculating a vertebrate with a plasmid-deficient strain of a *Chlamydia* species, wherein a wild-type disease-causing strain of the species contains a plasmid; wherein vertebrates inoculated with the plasmid-deficient strain show reduced pathology when later infected with the wild-type disease-causing strain of the *Chlamydia* species as compared to vertebrates not inoculated with the plasmid-deficient strain.

BRIEF DESCRIPTION OF THE DRAWINGS

FIG. 8 is a plot of quantitative IFU data obtained from cervicovaginal swabs of infected mice. Data points are the means±SD of mice found to be positive for infection on each day with 5 animals examined per group. Panel A, course and duration of primary infection; Panel B, course and duration of challenge infection (numbering reflects days since primary infection). The intensity and duration of challenge infection with Nigg was reduced compared to primary infection in all three groups, but this decrease was statistically significant only for mice primarily infected with Nigg, ($P<0.001$); ($P=0.05$ for mice primarily infected with CM972, and $P=0.18$ for mice primarily infected with CM3.1). Clearance of challenge infection with Nigg was delayed in mice primarily infected with the plasmid-deficient strains, ($P=0.02$ for Nigg/Nigg vs. CM3.1/Nigg; $P=0.05$ for Nigg/Nigg vs. CM972/Nigg; $P=0.03$ for CM3.1/Nigg vs. CM972/Nigg by two-way RM ANOVA).

FIG. 10. TNF-α in genital secretions of 5 C3H/HeN mice infected with Nigg (▲), CM972 (○), or CM3.1 (■) (Means±SD). $P=0.025$ for Nigg vs. CM3.1; $P=0.017$ for Nigg vs. CM972; $P=0.06$ for CM3.1 vs. CM972 (Two-way RM ANOVA).

DETAILED DESCRIPTION

Definitions

Figure 1:
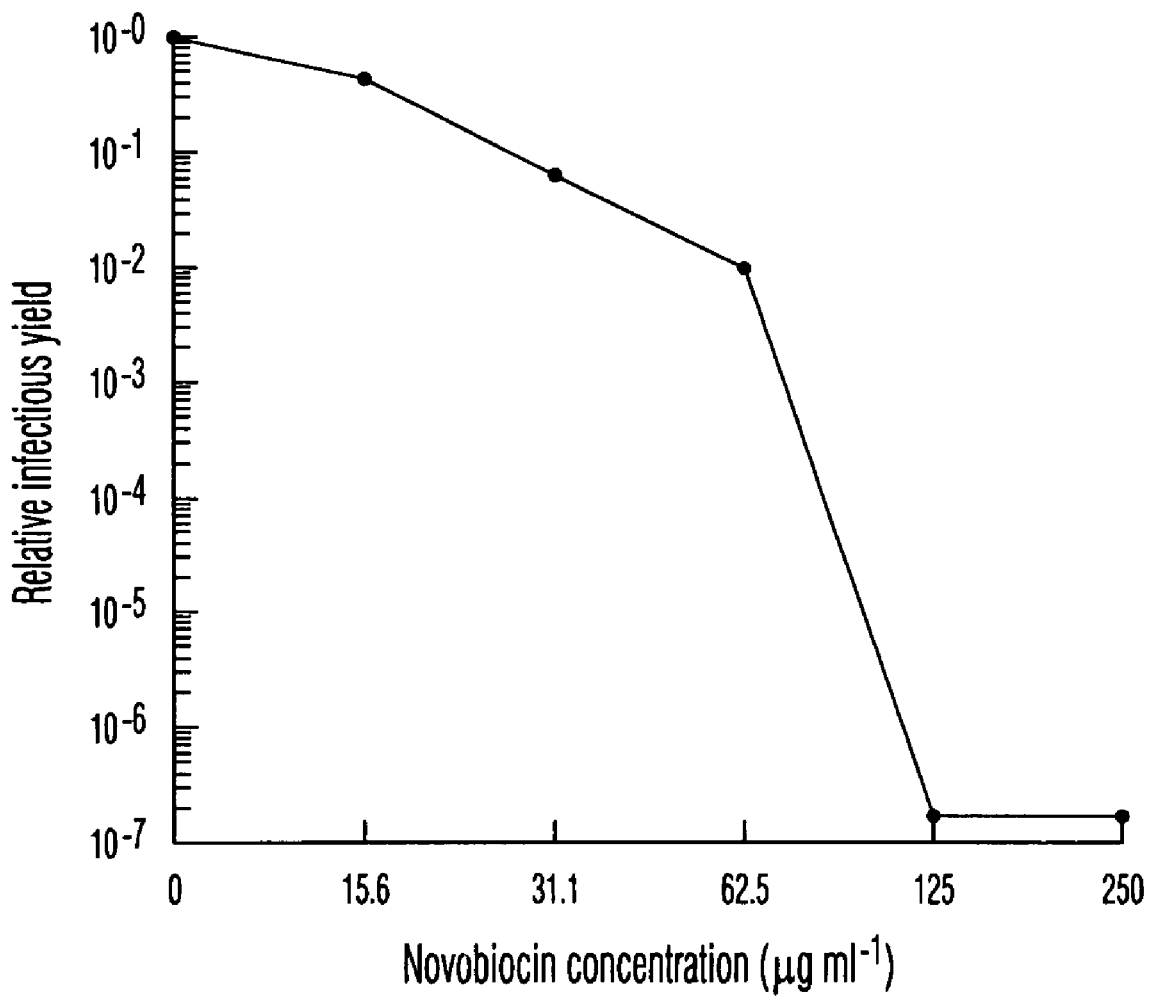
FIG. 1. Effect of novobiocin treatment on replication of *C. muridarum* strain Nigg. The novobiocin-treated Chlamydiae were harvested and plated by centrifugation to generate individual plaques for titration. The relative infectious yield of strain Nigg at each novobiocin concentration was derived by normalizing the total infectious yield per treated population against the yield from the untreated control. The graph is drawn from a single representative experiment with each point assayed in duplicate.

"Efficiency of Plaquing" (EOP), or plaquing efficiency, for a given strain is defined as (Number of plaques formed under a certain condition)/(Inclusion forming units formed under the most permissive condition tested for infection). Assays for inclusion forming units and plaque forming units are described in Example 1 below.

"Relative Plaquing Efficiency" is defined as (the EOP of strain 1 under a certain condition)/(EOP of strain 2 under the same condition).

"Permissive" and "nonpermissive" conditions are defined relative to each other. The plaquing efficiency of a plasmid-deficient *Chlamydia* strain is higher in permissive conditions than nonpermissive conditions. The relative plaquing efficiency of a plasmid-deficient strain with low infection efficiency as compared to the plaquing efficiency of the corresponding wild type plasmid-containing strain (EOP of plasmid-deficient strain/EOP of plasmid-containing strain) is also higher in permissive conditions than in nonpermissive conditions. Preferably, the relative plaquing efficiency is at least 10-fold higher in the permissive conditions than the nonpermissive conditions, and more preferably at least 50 fold higher.

A "highly infective plasmid-free *Chlamydia* sp. strain" refers to a strain of plasmid-free *Chlamydia* sp. that is more infective than most comparable plasmid-free *Chlamydia* sp. strains (e.g., a parent plasmid-free strain that it is derived from) and preferably but not necessarily approximately as infective as (or more infective than) comparable plasmid-containing wild type *Chlamydia* sp. strains.

The term "plasmid-deficient strain of *Chlamydia* sp." refers to a strain that is lacking the plasmid found in a corresponding wild-type similar *Chlamydia* sp. strain. Typically, the plasmid-deficient strain is isolated by curing a parent plasmid-containing strain of its plasmid. Some plasmid-deficient strains may contain a plasmid other than the plasmid found in most wild-type similar strains, e.g., a foreign recombinant vector plasmid.

The term "a corresponding plasmid-containing strain" refers to a *Chlamydia* sp. strain otherwise similar to a plasmid-deficient strain but containing a *Chlamydia* plasmid. Typically, the "corresponding plasmid-containing strain" is a parental strain from which the plasmid-deficient strain is derived by curing the parental plasmid-containing strain of its plasmid.

Description:

The invention involves the discovery that plasmid-cured *Chlamydia* (shown with specifically *C. muridarum* Nigg) have a decreased infectivity and produce smaller plaques than the corresponding plasmid-containing wild type strain. The decreased infection efficiency can be partially overcome by centrifuging the plasmid-deficient *Chlamydia* onto host cells at low g forces, e.g., 1,600×g to enhance infection. Other treatments may also enhance infection efficiency for plasmid-deficient *Chlamydia*, such as the use of DEAE-Dextran (Sabet et al. 1984).

Thus, plasmid-deficient *Chlamydia* can be isolated by treating *Chlamydia* under plasmid-curing conditions and then incubating the treated *Chlamydia* with host cells under conditions permissive for infection by plasmid-deficient *Chlamydia*, e.g. with centrifuging the treated *Chlamydia* onto host cells.

Curing *Chlamydia* of plasmids can be accomplished by culturing in novobiocin at sublethal doses, i.e., a dose that reduced infection by approximately 99%. Other agents and treatments have also been used to cure other bacteria and presumably would be effective with *Chlamydia*, including culturing with sublethal doses of acriflavin, sodium dodecyl sulfate (SDS), sarkosyl, and ethidium bromide (Chin et al. 2005). Electroporation may also be used to cure bacteria of plasmids.

After treating plasmid-containing *Chlamydia* under plasmid-curing conditions, the treated bacteria are incubated with host cells under conditions permissive for infection by plasmid-deficient *Chlamydia*. Then the chlamidiae are cultured in the host cells and plaques are isolated from the host cells. Plasmid-free isolates generally produce smaller plaques, so it is preferable to select small plaques for isolation.

Next, one verifies that the isolated plaques are plasmid-deficient. This may involve as a first step expanding the isolate by culture in host cells to yield a higher titer for subsequent analysis. The isolates can then be cultured in host cells and inclusions produced in the host cells can be stained with iodine to test for glycogen. Plasmid-deficient *Chlamydia* are found herein to not produce glycogen-containing inclusions, while plasmid-containing strains do produce glycogen-containing inclusions. PCR with primers specific for a plasmid gene, such as pMoPn F2/R2, described in Example 1, can be used to verify the absence of the plasmid. The sequences of the plasmid in several strains of *Chlamydia* have been sequenced, e.g., GenBank accession numbers X07547 and CP000052 for *C. trachomatis* and AE002162 for *C. muridarum* Nigg. These can be used to select primers for plasmid detection by PCR or by southern blotting. The complete genome of several *Chlamydia* sp. are also available, e.g., AE001273 for *C. trachomatis* strain D/UW-3/CX, AE002160 for *C. muridarum* strain Nigg. Knowledge of chromosomal sequences can be used to design control primers for detection of chromosomal DNA by PCR or southern blotting.

The plasmid-deficient *Chlamydia* strains, such as CM972, generally have low infectivity, and therefore steps to enhance infectivity such as centrifugation are necessary to efficiently infect host cells. But starting from an isolated plasmid-deficient strain with low infectivity, it is possible to isolate a plasmid-deficient mutant strain with high infectivity by selecting for more infective variants or allowing plaques to form and harvesting plaques larger than typical plaques formed by the parent plasmid-deficient strain. It is found below that CM972, a typical plasmid-deficient strain, has reduced infection efficiency and forms small plaques. A variant derivative of it, CM3.1, which has higher infection efficiency similar to wild type also forms larger plaques similar in size to the wild type plasmid-containing strain. Thus, large plaques appear to correlate with normal infection efficiency.

One method of developing a highly infective plasmid-deficient strain is to infect host cells under conditions that are nonpermissive for infection by the parent plasmid-deficient *Chlamydia* strain, such as incubating host cells with the bacteria without centrifugation. Under these conditions, a substantial fraction of plaques formed in the host cells will be a more infective mutant derivative, rather than the parent plasmid-deficient strain. Plaques can be picked and characterized to measure their infection efficiency to verify that a plaque contains a highly infective variant strain. By picking larger plaques, the likelihood of finding a highly infective strain is also increased.

The process for developing a highly infective plasmid-deficient *Chlamydia* sp. strain in some embodiments involves infecting host cells in vitro with the parent plasmid-deficient *Chlamydia* strain, allowing plaques to form, and harvesting one or more plaques larger than typical plaques formed by the one or more parent plasmid-deficient *Chlamydia* strains to isolate the one or more highly infective plasmid-deficient *Chlamydia* sp. strains. The infection of the host cells is preferably under non-permissive conditions, such as without centrifugation, to select for highly infective variants. But it may be under permissive conditions, such as with centrifugation onto host cells. Picking larger plaques is still likely to result in isolation of a highly infective strain.

The process for developing a highly infective plasmid-deficient *Chlamydia* sp. strain preferably involves measuring infection efficiency in vitro or in vivo of the one or more highly infective plasmid-deficient *Chlamydia* sp. strains to verify that the one or more highly infective strains have a higher infection efficiency than the one or more parent strains.

To identify a *Chlamydia* sp. strain suitable for use as a vaccine, one or more plasmid-deficient *Chlamydia* strains are isolated as described above or otherwise obtained. Then a vertebrate (e.g., a mammal or bird) is inoculated with the one or more plasmid-deficient *Chlamydia* sp. strains and any pathologic sequelae caused by the strains are characterized and any immune response in the vertebrate to the strains is characterized to identify a strain suitable as a vaccine.

In some embodiments, the method further involves incubating host cells with the one or more plasmid-deficient *Chlamydia* sp. strains to infect the host cells and selecting for more infective *Chlamydia* sp. variants or allowing plaques to form and harvesting one or more plaques larger than typical plaques formed by the one or more plasmid-deficient *Chlamydia* strains to isolate one or more highly infective plasmid-deficient *Chlamydia* sp. strains. The vertebrate is then inoculated with the one or more highly infective plasmid-deficient *Chlamydia* sp. strains.

The step of isolating one or more highly infective plasmid-deficient strains may involve incubating host cells with the one or more plasmid-deficient *Chlamydia* sp. strains under conditions that are nonpermissive for infection by the plasmid-deficient *Chlamydia* sp. strains and selecting for *Chlamydia* that infect the host cells to isolate one or more highly infective plasmid-deficient *Chlamydia* sp. strains. It can further or alternatively involve allowing plaques to form and harvesting one or more plaques larger than typical plaques formed by the one or more plasmid-deficient *Chlamydia* sp. strains to isolate one or more highly infective plasmid-deficient *Chlamydia* sp. strains.

Preferably, a suitable vaccine strain causes reduced pathology as compared to a corresponding plasmid-containing disease-causing *Chlamydia* strain in the vertebrate and elicits a protective immune response that rids the vertebrate of the infective plasmid-free strain. This is true of strain CM3.1 described in Example 3 below. It caused less inflammation and other symptoms in mice than the wild-type strain, and persisted over the same time course as the wild-type strain before being cleared from the mice, presumably by a protective immune response.

Preferably, the process of developing a strain suitable for use as a vaccine also includes measuring multiplication or persistence of the plasmid-deficient *Chlamydia* strain. Preferably, the plasmid-deficient *Chlamydia* strain is able to persist in the vertebrate over a time course sufficient to allow a protective immune response to develop. In particular embodiments, the multiplication or persistence of the plasmid-deficient *Chlamydia* strain in the mammal is compared to the multiplication or persistence of a plasmid-containing disease-causing strain in the mammal and the plasmid-deficient strain persists with at least 1% or at least one-fifth as many Inclusion Forming Units as the plasmid-containing disease-causing strain for at least 5 days or at least 10 days after inoculation of the mammal.

In some embodiments of the process of identifying a strain of *Chlamydia* sp. suitable for use as a vaccine the step of characterizing any pathological sequelae the plasmid-deficient strains cause and any immune response they cause includes characterizing the response of the vertebrate to infection by a disease-causing plasmid-containing *Chlamydia* sp. strain corresponding to the one or more plasmid-deficient *Chlamydia* sp. strains after inoculating the vertebrate with the one or more plasmid-deficient *Chlamydia* strains.

Preferably the process of identifying a strain of *Chlamydia* sp. suitable for use as a vaccine identifies one or more plasmid-deficient strains that cause reduced pathology as compared to a corresponding plasmid-containing disease-causing *Chlamydia* strain in the vertebrate and cause a protective immune response in the vertebrate that rids the vertebrate of the plasmid-deficient *Chlamydia* strain.

Preferably the process of identifying a strain of *Chlamydia* sp. suitable for use as a vaccine identifies one or more plasmid-deficient *Chlamydia* strains that cause reduced pathology as compared to a corresponding plasmid-containing disease-causing *Chlamydia* strain in the vertebrate; and wherein following inoculation with the one or more identified plasmid-deficient *Chlamydia* strains, when a vertebrate is infected with the corresponding disease-causing strain the vertebrate experiences reduced pathology as compared to a vertebrate not previously inoculated with the one or more identified plasmid-deficient *Chlamydia* strains.

In some embodiments the vaccine strain is a highly infective plasmid-deficient *Chlamydia* strain.

Characterizing the host immune response includes measuring concentrations of cytokines such as tumor necrosis factor (TNF), macrophage inflammatory protein-2 (MIP-2), interleukin-8 (IL-8), and gamma interferon. Preferably, a suitable vaccine strain causes secretion of gamma interferon, which promotes and is indicative of a protective T-cell response, and does not induce proinflammatory cytokines such as TNF and IL-8, and MIP-2, which is the mouse equivalent of human IL-8. Anti-*Chlamydia* antibodies may also be produced, but are not thought to be protective. An effective protective response depends on T-cells, so an important parameter that may be monitored is the development of CD4 T-cells that proliferate in response to *Chlamydia* antigens. Proliferative response of CD4 T-cells and other peripheral blood mononuclear cells can be monitored as described in U.S. patent application Ser. No. 11/061,996 and Pinto et al. 2003.

Kits for detecting and quantifying these cytokines are available from R & D Systems, Inc., Minneapolis, Minn. (www.rndsystems.com).

Indications of likely host immune response can also be obtained in vitro. As in Example 3 below, host cells are infected in vitro with *Chlamydia* and the infected culture is assayed for IL-8 production. Low IL-8 production is predictive of a good vaccine strain that does not induce pathologic sequelae since IL-8 is a pro-inflammatory cytokine and inflammation correlates with pathological symptoms. Production of other cytokines such as TNF and gamma-interferon can also be measured with in vitro infection. Among the cytokines, lowered IL-8 production is particularly significant as a marker for reduced pathology because expression of this cytokine is regulated by TLR2 (a Toll-like receptor), and it has been demonstrated that mice lacking TLR2 have no reproductive tract pathology after infection with *C. muridarum* Nigg (Darville et al. 2003).

Thus, another embodiment of the process for developing a strain of *Chlamydia* sp. suitable for use as a vaccine involves infecting mammalian host cells in vitro with the plasmid-deficient *Chlamydia* sp. strain and measuring production of one or more inflammatory or immunomodulatory cytokines by the mammalian host cells.

Another embodiment of the invention provides a method of expressing a recombinant nucleic acid in *Chlamydia* comprising: (a) obtaining a plasmid-deficient *Chlamydia* sp. strain; (b) incubating the plasmid-deficient *Chlamydia* with a plasmid of *Chlamydia* origin comprising a recombinant nucleic acid to generate a pool of potentially transformed *Chlamydia* cells; and (c) isolating transformed *Chlamydia* carrying the plasmid comprising the recombinant nucleic acid.

Preferably the step of isolating transformed *Chlamydia* comprises incubating host cells with the pool of potentially transformed *Chlamydia* cells under conditions that are non-permissive for infection by the plasmid-deficient *Chlamydia* sp. strain and selecting for *Chlamydia* that infect the host cells. In one embodiment, the conditions nonpermissive for infection by the plasmid-deficient *Chlamydia* sp. strain are incubating the host cells without centrifuging the *Chlamydia* cells into the host cells.

The step of isolating transformed *Chlamydia* may also or alternatively involve allowing plaques to form in host cells and harvesting one or more plaques larger than typical plaques formed by the plasmid-deficient *Chlamydia* strain.

The step of isolating transformed *Chlamydia* may also involve identifying *Chlamydia* plaques that accumulate glycogen within their intracytoplasmic inclusions.

One embodiment of the invention provides a method of immunizing a vertebrate against a disease-causing *Chlamydia* infection involving: inoculating a vertebrate with a plasmid-deficient strain of a *Chlamydia* species, wherein a wild-type disease-causing strain of the species contains a plasmid; wherein vertebrates inoculated with the plasmid-deficient strain show reduced pathology when later infected with the wild-type disease-causing strain of the *Chlamydia* species as compared to vertebrates not inoculated with the plasmid-deficient strain.

In specific embodiments, the plasmid-deficient strain is a derivative of the wild-type disease-causing strain.

In particular embodiments, the plasmid-deficient strain does not induce glycogen inclusions in vertebrate cells, and the wild-type disease causing strain does induce glycogen inclusions in vertebrate cells.

In particular embodiments, the plasmid-deficient strain has reduced infectivity in vitro as compared to the corresponding plasmid-containing strain.

In particular embodiments, the *Chlamydia* species is *C. muridarum*. In other embodiments, the *Chlamydia* species is *C. psittaci, C. trachomatis*, or *C. pneumoniae*.

The invention will now be illustrated with the following Examples, which are intended to illustrate the invention but not limit its scope.

EXAMPLES

Example 1

**A Plasmid-Cured *C. muridarum* Strain Displays Altered Plaque Morphology and Reduced Infectivity in Cell Culture**

Currently, a genetic system for use in Chlamydiae is lacking. A better understanding of the mechanisms by which the cryptic plasmid, a potential gene delivery vector, is maintained, and the ability to generate at high efficiency plasmid-deficient derivatives of the most highly characterized Chlamydiae for use as recipient strains would advance progress in this area. This example describes the curing of the mouse-virulent *C. muridarum* using novobiocin. Characterization of the cured strain revealed, in addition to the inability to accumulate glycogen, an in vitro attachment or uptake defect that could be partially overcome by centrifugation.

Methods:

Strains, cell lines and culture conditions: The Chlamydial strains used in the course of this study are indicated in Table 1. Cell culture media and reagents were purchased from Mediatech (Hearndon, Va.). Wells containing confluent monolayers of McCoy cells were infected at an approximate MOI of 0.5-1, before being centrifuged for 1 hour at 37° C. The infective inoculum was then removed and replaced with 1× Dulbecco's modified Eagle's medium (DMEM) supplemented with 10% heat-inactivated FBS, gentamicin (20 μg $ml^{-1}$) and 0.1 μg $ml^{-1}$ cycloheximide. We have previously determined that concentrations in excess of 250 μg $ml^{-1}$ are cytotoxic for uninfected McCoy cells. Novobiocin (Sigma, St. Louis, Mo.) was added at the indicated concentrations (up to 250 μg $ml^{-1}$) at 4 hours post infection. Infected cells were incubated at 37° C., 5% $CO_2$ for a further 36 hours. Infected cells were harvested into SPG buffer (218 mM sucrose, 3.8 mM $KH_2PO_4$, 7.2 mM $K_2HPO_4$, 4.9 mM L-glutamate, pH 7.2) at 40 hours post infection, sonicated, and stored at −80° C. Bacteria were subsequently titrated by plaque assay or as inclusion forming units (IFU) using a genus-specific fluorescently tagged monoclonal antibody (Biorad, Hercules, Calif.).

TABLE 1

Bacterial strains used in this Example.

| Strain | Description | Source or Reference |
|---|---|---|
| *C. muridarum* Nigg | Wild type, mouse virulent. | Nigg 1942 |
| *C. muridarum* CM972 | Plasmid-deficient derivative of strain Nigg. | This study |
| *C. trachomatis* 25667R | Plasmid-deficient clinical isolate, serovar L2 | Peterson et al. 1990 |
| *C. trachomatis* CT599 | Plasmid-deficient clinical isolate, serovar E | Stothard et al. 1998 |

Plaque forming assay. Dilutions of the freshly harvested, novobiocin-treated bacteria were inoculated by centrifugation at 1,600×g for 1 hour at 37° C. onto confluent monolayers of McCoy cells grown in 6 well tissue culture dishes. The infective inoculum was then removed and the monolayers were overlaid with 1×DMEM, 10% FBS, 0.25% agarose, 0.01 μg $ml^{-1}$ cycloheximide and incubated at 37° C., 5% $CO_2$ for five days, to allow plaques to form. To visualize plaques, the solid overlay was removed and the monolayer stained with 0.025% Neutral Red in 1×PBS. Plaque purifications were carried out by picking individual plaques into 200 μl of SPG buffer. These plaque suspensions were then sonicated to lyse the cells and appropriate dilutions replated in the plaque assay. Amplification of plaques arising after novobiocin treatment, or of sequentially plaque-purified isolates was achieved by the picking of individual plaques as described above, then using this material to infect, via centrifugation, individual wells of a 24 well dish containing confluent monolayers of McCoy cells and passing through a single round of synchronous infection before harvesting in SPG buffer. An additional passage was performed in an identical manner using ~1:100 of the well harvest as inoculum. These sequential rounds of infection usually resulted in stocks at ~1-2×$10^8$ IFU $ml^{-1}$ that were then used for further analysis.

Inclusion forming units (IFU). To calculate plaquing efficiency, the number of inclusion forming units in an inoculum was determined as described in Kelly et al., 1996. Individual wells of McCoy cell monolayers in 96-well plates were inoculated with 200 μl of a solution containing *Chlamydia* followed by centrifugation at 1600×g for 1 hour. The plates were then incubated for 2 hours at 37° C. At this time, the solutions were removed and fresh medium was added and plates were incubated for another 32 hours at 37° C. The cultures were then fixed with methanol. *Chlamydia* inclusions were identified by addition of anti-*Chlamydia* immune sera and anti-mouse IgG conjugated to fluorescein isothiocyanate. The number of inclusions within 20 fields (40×) was counted under a fluorescent microscope, and inclusion-forming units per ml were calculated.

Iodine staining of *Chlamydia*-infected cells. McCoy cells cultured on glass cover slips were infected as described above. At the desired point in the infection the culture medium was removed and the monolayer rinsed several times with 1×HBSS before being fixed and stained with iodine (Schachter J & Dawson, 1978) in order to detect the presence of accumulated glycogen. Stained cells were immediately photographed using a digital camera system and SPOT version 4.0.6 software from Diagnostic Instruments Inc. (Sterling Heights, Mich.).

Detection of Chlamydial plasmid or chromosome by PCR. Genomic material was routinely prepared for use as PCR template by boiling Chlamydial suspensions containing $10^7$ IFU $ml^{-1}$ or greater for 10 minutes, then diluting 10 fold in distilled $H_2O$. PCR amplifications were performed using 5 μl of this preparation in a 20 μl reaction volume. Template preparations were amplified as follows, 95° C. 30 sec, 50° C. 30 sec, 72° C., 30 sec for 40 amplification cycles using the primer pairs described in Table 2.

TABLE 2

PCR primers used in this study.

| Name | Sequence | Product Size (bp) |
|---|---|---|
| tufA F4 (sense primer) | 5' CACTACGCTCACGTGGACTG 3' (SEQ ID NO: 1) | 593 |

TABLE 2-continued

PCR primers used in this study.

| Name | Sequence | Product Size (bp) |
| --- | --- | --- |
| tufA R4 | 5' CTCTCCTGCACGACCTTCTG 3' (SEQ ID NO: 2) | |
| pMoPn F2 (sense primer) | 5' TGTCACAGCGGTTGCTCTAA 3' (SEQ ID NO: 3) | 317 |
| pMoPn R2 | 5' CTATGCTGCAAGGAGGTAAG 3' (SEQ ID NO: 4) | |

Results:

Effect of novobiocin treatment on replication of Chlamydiae. Treatment with sub-lethal doses of novobiocin can influence the extent of DNA supercoiling (Luttinger, 1995), impacting gene expression and rendering the antibiotic an effective plasmid-curing agent (Gado et al., 1987; Hooper et al., 1984; Wolfson et al., 1983). Thus we were interested in investigating the possibility that novobiocin treatment might enhance the rate of plasmid loss from C. trachomatis. We titrated the impact of increasing amounts of novobiocin on Chlamydial growth using C. muridarum Nigg (Nigg, 1942), a strain that previously had not been demonstrated to be curable. Increasing amounts of freshly diluted novobiocin were added to the cell culture medium 4 hours post infection. The titers of novobiocin-treated bacteria were measured by plaque assays (FIG. 1). Although the impact of drug treatment on the recovery of infectious Chlamydiae was minimal at the lowest amounts, novobiocin concentrations of 62.5 µg ml$^{-1}$ reduced the relative infectious yield of bacteria by at least 100-fold. By extrapolation from other microorganisms (Gado et al., 1987; Hooper et al., 1984; Wolfson et al., 1983), we anticipated that plasmid curing would be most effective at concentrations where ~99% of bacterial growth was inhibited by the antibiotic.

Figure 2A:
FIG. 2. Characterization of plasmid-deficient derivatives of *C. muridarum*. Panel A, live McCoy cells, inoculated with strain CM972 were photographed 40 hours after infection at 400× magnification using phase contrast microscopy to reveal intracytoplasmic inclusions. Panel B, represents the results of PCR screening for the presence of the cryptic plasmid. Equal amounts of template were added to PCR reactions containing either primers directed against the cryptic plasmid (pMoPN F2/R2), or the Chlamydial genome (tufF4/R4). Panels C, D. McCoy cells infected with either strain Nigg (C) or strain CM972, the plasmid-deficient derivative (D), were fixed and stained with the strain-specific mouse monoclonal M40 24 hours post infection. The monoclonal antibody was then detected using a goat, anti-mouse FITC conjugated antibody with simultaneous Evans Blue staining of cytoplasm before being photographed at 1000× magnification.
Figure 2B:
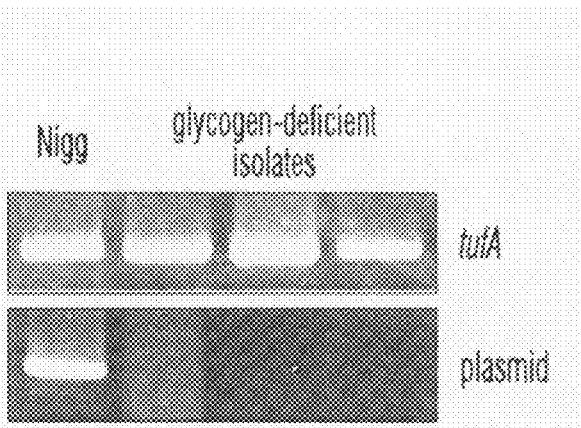
Figure 2C:
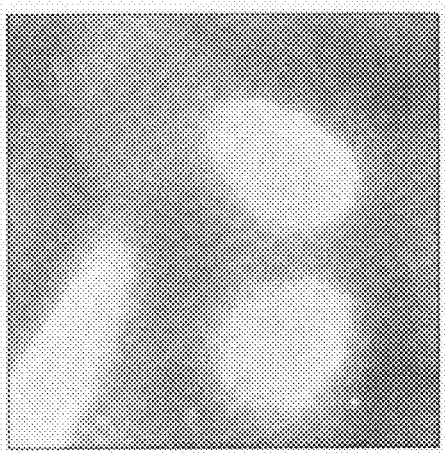
Figure 2D:
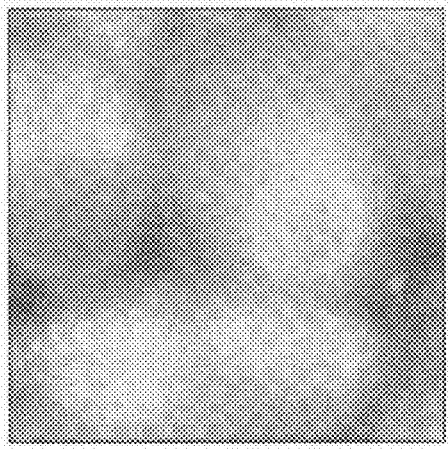
Figure 3A:
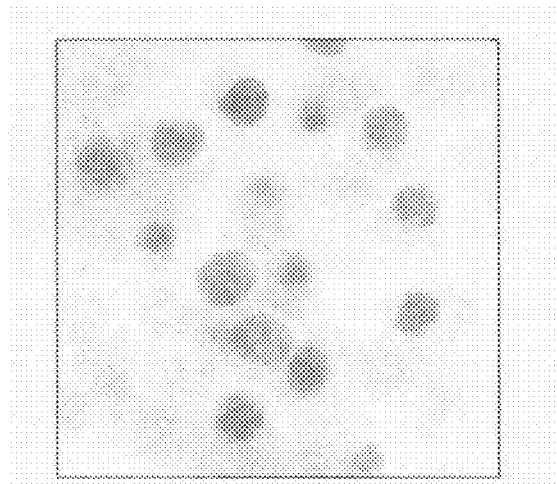
FIG. 3. Glycogen accumulation by *C. muridarum* Nigg is sensitive to novobiocin treatment and is not observed in strain CM972, a plasmid-deficient derivative. Panel A, B, McCoy cells were infected with *C. muridarum* Nigg, then treated with 62.5 µg ml$^{-1}$ novobiocin 4 hours post infection (panel B) or negative control (panel A). The infected cells were fixed and stained with iodine 40 hours post infection before being photographed at 400× magnification. Panel C, McCoy cells infected with *C. muridarum* strain CM972 were also fixed and stained with iodine at 40 hours post infection before being photographed at 1000× magnification. Arrows indicate the location of Chlamydial inclusions with altered or absent glycogen accumulation. Scale bar=15 μm.
Figure 3B:
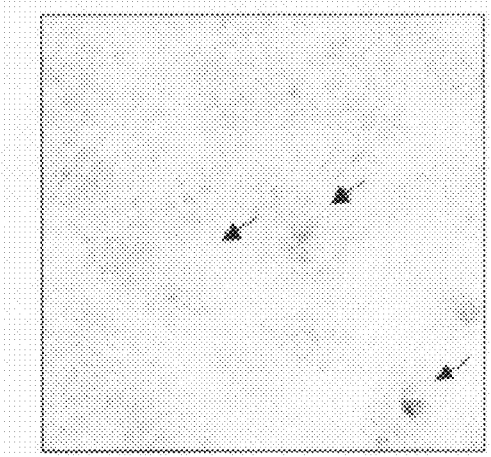
Figure 3C:
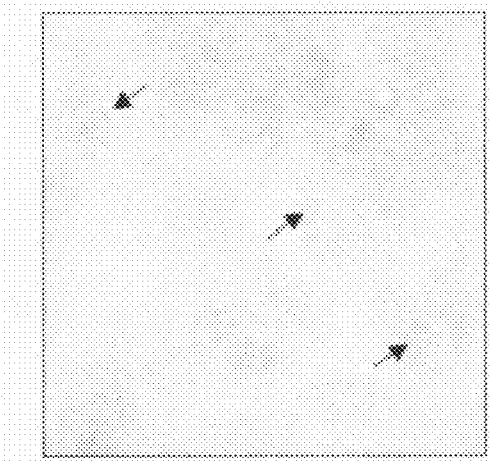

To examine whether novobiocin treatment had cured the plasmid, individual plaques were picked from the 62.5 µg ml$^{-1}$ plate, where we had observed the desired rate growth inhibition and thus might expect optimal plasmid curing, and passaged as described above. The isolates were then sequentially plaque purified 3-5 times, before being re-amplified via synchronous passage to high titer. Each of the plaque-purified isolates was then screened by PCR for the presence of the cryptic plasmid. A chromosome-specific target, the tufA gene that encodes the elongation factor Ef-Tu involved in protein biosynthesis, was used as control. A plasmid-specific PCR product was not obtained from isolates at a frequency that ranged from 4 to 30% (1 of 24:8 of 24) even though each yielded a tufA product from the same amount of template (FIG. 2b). In contrast, plaques picked and amplified from the untreated control plate failed to yield any plasmid-deficient isolates (0 of 51:0 of 18). The absence of plasmid was confirmed by Southern hybridization using a plasmid-specific probe (data not shown). A single representative of the plasmid-deficient isolates was then selected for continued analysis and designated C. muridarum strain CM972.

Figure 4:
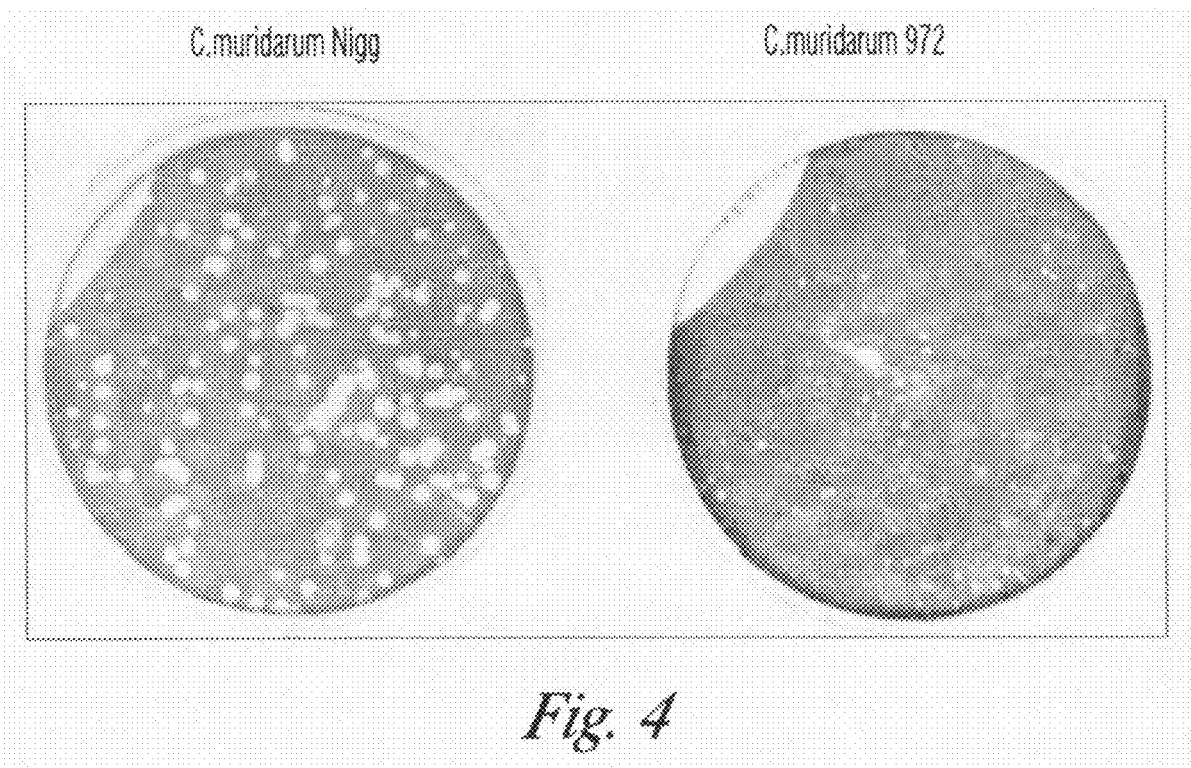
FIG. 4. Plaques formed by plasmid-deficient *C. muridarum* are reduced in size. Single plaques formed by *C. muridarum* strains Nigg and CM972 in McCoy cell monolayers grown in 35 mm diameter dishes after 5 days incubation at 37° C., 5% $CO_2$. The solid overlay was removed and the cells stained with Neutral Red before being photographed.
Figure 5:
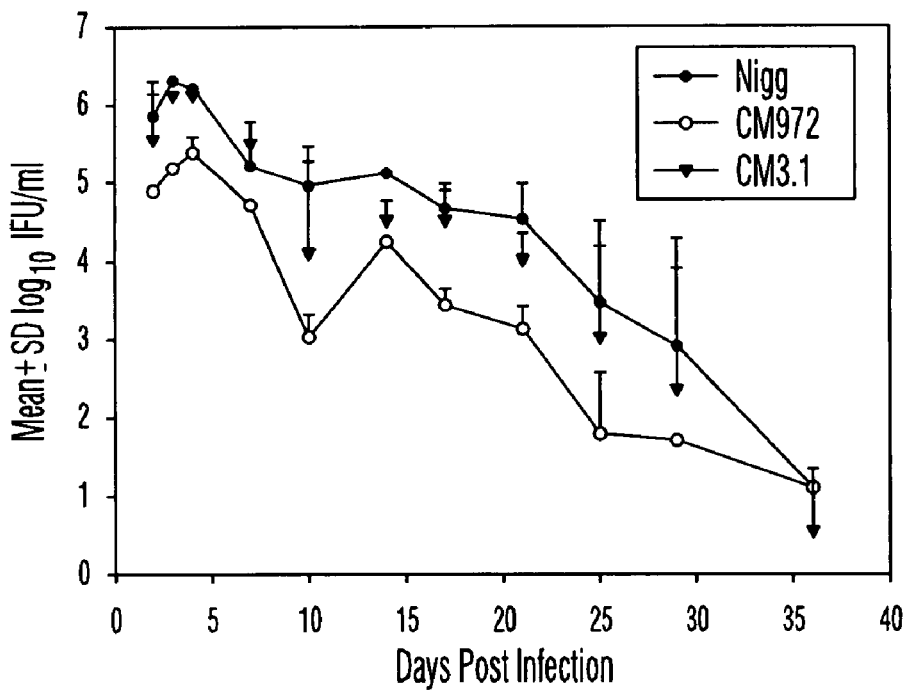
FIG. 5 is a plot of infectious chlamydiae (log IFU) shed from the lower genital tract of mice after infecting with *C. muridarum* Nigg, CM3.1, or CM972.
Figure 6:
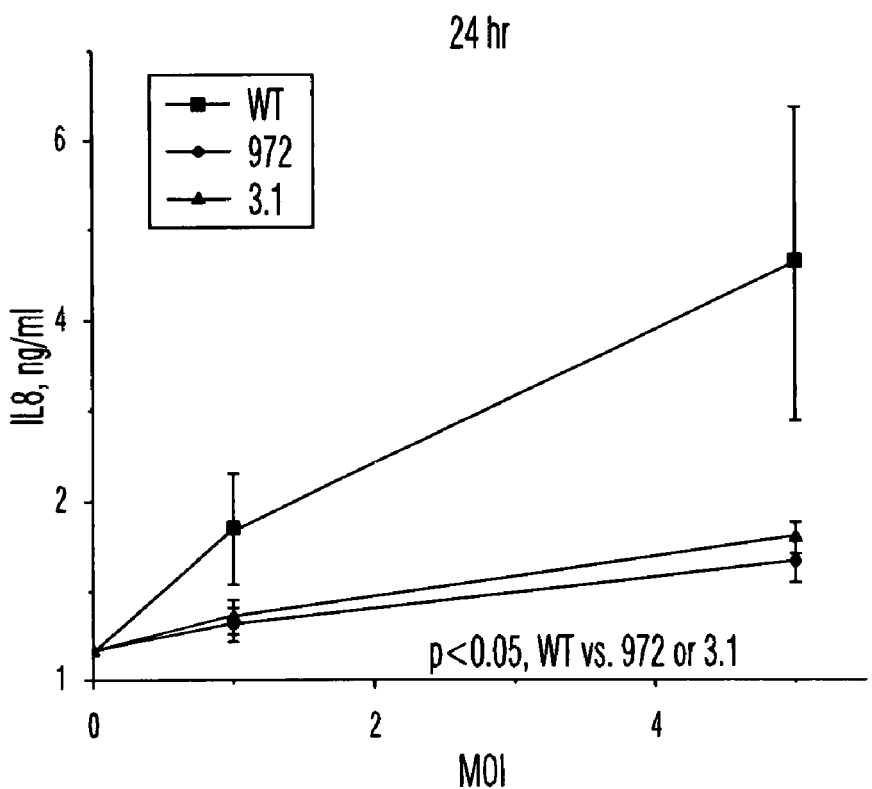
FIG. 6 is a plot of concentration of IL-8 (interleukin-8) secreted into the culture supernatant by cells infected with *C. muridarum* Nigg (wt), CM3.1, or CM972 at 24 hours post-infection.
Figure 7:
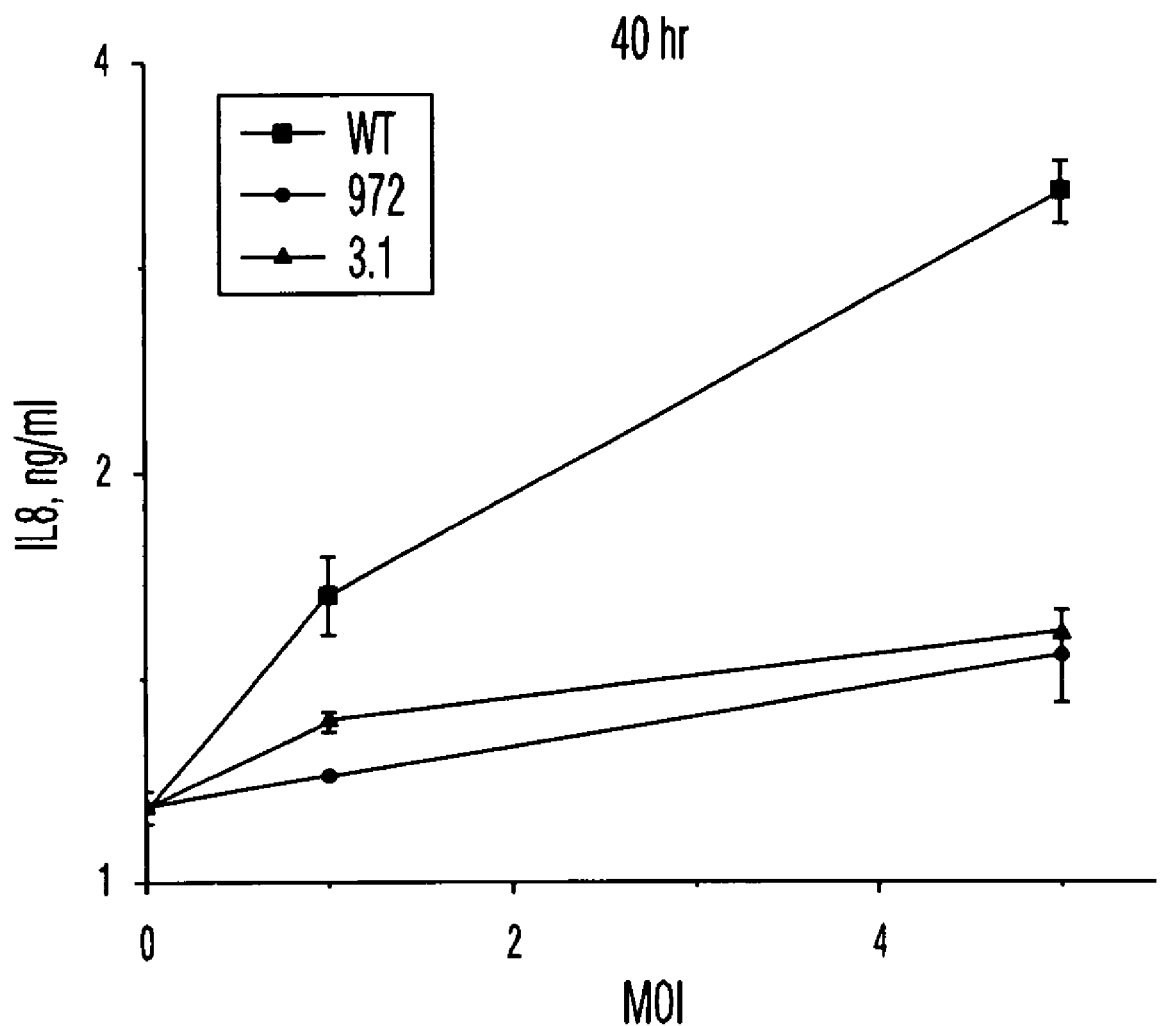
FIG. 7 is a plot of concentration of IL-8 secreted into the culture supernatant by cells infected with *C. muridarum* Nigg (wt), CM3.1, or CM972 at 40 hours post-infection.

To confirm the parental background of strain CM972 we performed immunofluorescent staining of infected McCoy cells using the strain-specific mouse monoclonal antibody M40 that was obtained from Dr. Ellena Peterson (U.C. Irvine). This antibody is directed against a VD1 epitope of the major outer membrane protein (MOMP) expressed by C. muridarum Nigg. We observed that the bacteria within inclusions formed by both the Nigg and the plasmid-deficient CM972 stained positively (FIG. 2 c, d). The genome of C. muridarum Nigg has been sequenced (Read et al., 2000) so we further confirmed the identity of the CM972 by amplifying and sequencing a region of ompA, the gene that encodes MOMP, using the primer set BII and FII (Dean et al., 1995). The DNA sequence of the amplified fragment was identical to both the parental Nigg strain and the published sequence (data not shown).

Plasmid-deficient *C. muridarum* fail to accumulate glycogen within inclusions. Previously, the three plasmid-deficient strains isolated by Matsumoto et al., were shown to be unable to accumulate glycogen within the intracytoplasmic inclusions formed by the growing bacteria (Matsumoto et al., 1998). Staining of McCoy cells infected with either of the clinical isolates, *C. trachomatis* 25667R or CT599, known to lack the cryptic plasmid revealed that these strains too are unable to accumulate glycogen (data not shown). In contrast, *C. muridarum* strain Nigg stains positively with iodine by 28 hours post infection (FIG. 3*a*). Novobiocin treatment of Nigg-infected McCoy monolayers resulted in variable iodine staining of inclusions, ranging from non-staining inclusions to inclusions that appeared to contain only patchy depositions of iodine to inclusions which resembled those formed by untreated bacteria (FIG. 3*b*). Analyses of the 48 plaques from the initial drug-treated bacteria screens revealed that only isolates cured of the cryptic plasmid failed to accumulate glycogen. Plasmid-cured isolates after plaque purification consistently failed to accumulate glycogen (FIG. 3C), indicating that glycogen accumulation is controlled by the plasmid.

Plasmid-deficient *C. muridarum* form smaller plaques at reduced efficiency. While attempting to determine the effectiveness of novobiocin as a plasmid-curing agent we observed that when the drug-treated *C. muridarum* were plated in a plaque assay using manual agitation (Banks et al., 1970) to inoculate the monolayers, only iodine positive, plasmid-containing isolates were recovered. In contrast, if the bacteria were inoculated into the plaque assay via centrifugation, both plasmid-containing wild type and plasmid-deficient, iodine-negative isolates could be recovered. Furthermore, attempts to plaque the clinical isolates *C. trachomatis* 25667R and CT599 via manual agitation were unsuccessful. We reasoned that loss of the cryptic plasmid might be associated with a reduced ability to form a plaque. To test the efficiency with which *C. muridarum* Nigg and strain CM972 were able to form plaques the strains were titrated in parallel experiments by plaque assay using the two plating methods described above, manual agitation and centrifugation. The results of this experiment are shown in Table 3. The ability of strain Nigg to form plaques was reduced ~13 fold when not centrifuged as compared to with centrifugation of the inoculum into the confluent monolayers. However, a much more striking difference was observed for strain CM972, which was 4 fold less likely to form a plaque than the parental strain after centrifugation, and whose ability to plaque was reduced an additional 471 fold when the inoculum was simply incubated with the monolayers. In addition, plaques formed by strain CM972 were considerably smaller than those of the parental strain, even when the bacteria had been centrifuged into the monolayers (FIG. 4). To exclude the possibility that the differences in plaque size were due to a reduced ability to replicate within McCoy cells, we compared the infectious yield of both strains when grown in synchronous culture with an MOI of 0.5 and no difference was observed (Nigg: $3.45 \times 10^7 \pm 6.39 \times 10^6$ IFU ml$^{-1}$ vs. strain CM972: $4.24 \times 10^7 \pm 7.58 \times 10^6$ IFU ml$^{-1}$), suggesting that once inside the cell, both strains replicate and form infectious progeny equally well.

TABLE 3

Plaquing efficiency of C. muridarum strains Nigg and CM972 on McCoy cells.

| Strain | Efficiency Of Plating$^a$ | |
|---|---|---|
| | Centrifugation | Manual Agitation |
| Nigg | $4.95 \times 10^{-1} \pm 3.28 \times 10^{-1}$ | $1.38 \times 10^{-2} \pm 5.79 \times 10^{-3}$ |
| CM972 | $6.02 \times 10^{-1} \pm 2.35 \times 10^{-2}$ | $1.13 \times 10^{-4} \pm 7.15 \times 10^{-5}$ |

Values shown are the average of two independent experiments performed in duplicate and are expressed as the EOP ± SE. The EOP$^a$ was calculated by dividing the plaque forming units ml$^{-1}$ under each condition by the IFU ml$^{-1}$ (determined by centrifugation onto monolayers).

Discussion:

This Example describes the isolation of plasmid-deficient derivatives of C. muridarum strain Nigg, using novobiocin as a curing agent. Plasmid-deficient derivatives derived by this method resemble naturally occurring plasmid-deficient strains in their inability to accumulate glycogen within intracytoplasmic inclusions. In addition we describe a novel phenotype—poor plaquing efficiency—which is observed for all plasmid-deficient strains of *C. trachomatis.*

Novobiocin is an effective curing agent for Chlamydiae. The ability to cure *C. muridarum* strain Nigg would suggest that at higher concentrations of novobiocin, plasmid replication is sufficiently inhibited that plasmid-deficient isolates can be recovered and is in contrast to previous reports that at low concentrations of the drug (20 μg $ml^{-1}$ in conjunction with imipramine, 20 μg $ml^{-1}$), plasmid copy number increases (Pickett et al., 2005). The high concentrations of novobiocin required to suppress Chlamydial replication were striking. However, the *C. trachomatis* genome carries CT284, an open reading frame that encodes a probable phospholipase D (Stephens et al., 1998). This is a homolog of cls, the gene that encodes cardiolipin synthase in *E. coli*. The cls gene has been recognized as identical to the wild-type form of the nov allele (Tropp et al., 1995) and mutations in nov are associated with greatly enhanced novobiocin sensitivity. Thus the intrinsic resistance to novobiocin that we observed may be due to impermeability of the chlamydial outer membrane. The effective concentration of novobiocin for plasmid curing remained below concentrations of the drug that are cytotoxic to the eukaryotic host, enabling the enrichment of plasmid-deficient bacteria. The use of novobiocin as a plasmid-curing agent is highly effective and allows the recovery of plasmid-deficient derivatives at high frequency. This technique should be generally applicable to other *C. trachomatis* strains or other plasmid-containing *Chlamydia* sp.

Plasmid-deficient Chlamydiae are less able to form plaques in cell culture. The data indicate that a reduced ability to form plaques in cell culture is associated with plasmid loss from *C. trachomatis*. Previously identified plasmid-deficient clinical isolates (Peterson et al., 1990; Stothard et al., 1998) that are available for study, also failed to plaque in our assay. However, the absence of an isogenic, plasmid-containing parental control for these clinical isolates made the significance of these observations difficult to interpret. Our observations that plasmid-deficient isolates were only recovered after novobiocin treatment if the bacteria were passed via centrifugation at all steps are consistent with those of Matsumoto et al., (Matsumoto et al., 1998) who reported the recovery of plasmid-deficient derivatives of in vitro cultured strains with little difficulty. It is noteworthy that centrifugation of the inoculum onto the cells was an integral component of all screening and passage steps in their protocols. The striking reduction in plaquing efficiency demonstrated by strain CM972 suggests that plasmid-deficient derivatives will be selected against using standard passaging techniques and even more so when plaque assay protocols that do not involve centrifugation of the monolayer are used for isolation and screening. Indeed, the variable recovery rates of cured derivatives after novobiocin treatment that we observed may reflect a bias on our part for smaller plaques when screening.

The role of the cryptic plasmid in Chlamydiae. Loss of the plasmid is associated with two distinct and possibly unrelated phenotypes (loss of glycogen accumulation, and reduced plaque efficiency), raising the possibility that a regulator of genes important for these phenotypes may be encoded on the plasmid. Nonetheless, the significance of these phenotypes to chlamydial infection is unclear. We have observed that a variety of environmental factors can suppress the accumulation of glycogen within inclusions, including ampicillin treatment and substrate limitation (data not shown). Furthermore, it should be noted that neither *C. psittaci*, nor *C. pneumoniae* accumulate glycogen within their inclusions, although the majority of *C. psittaci* and some *C. pneumoniae* strains carry the plasmid (Lusher et al., 1989), (Thomas et al., 1997), (McClenaghan et al., 1988) and the glycogen metabolic genes have been retained on the chromosome (Read et al., 2000; Read et al., 2003; Kalman et al., 1999). Although it has been noted that centrifugation of the Chlamydial inoculum onto cell monolayers can increase the efficiency with which cells may become infected (Rota, 1977; Lee, 1981; Pearce et al., 1981; Table 3), it is difficult to envisage how this manipulation might mimic a relevant in vivo condition.

Example 2

Isolation of a Plasmid-Less *C. muridarum* Strain with Normal Infectivity and Plaque Size The isolation of *C. muridarum* strain CM972 by plasmid curing of *C. muridarum* strain Nigg is described in Example 1. *C. muridarum* CM972 is a plasmid-deficient strain that forms small plaques and infects cells in tissue culture at very low efficiency in the absence of centrifugation. *C. muridarum* CM972 was plated on confluent McCoy cell monolayers at a multiplicity of 1-2 and incubated for 2 hours at 37° C. without centrifugation before being overlaid with 1×DMEM, 10% FBS, 0.25% agarose, 0.01 μg $ml^{-1}$ cycloheximide. The monolayers were incubated at 37° C., 5% $CO_2$ for 5-7 days, to allow plaques to form. Under these culture conditions, *C. muridarum* CM972 forms only tiny plaques and at low frequency. However, large plaques resembling those formed by *C. muridarum* Nigg were observed occurring at a frequency of 1-2×

$10^6$. The plaques were harvested, and individually purified by repeating the plaquing procedure 3 times before being expanded. Subsequent determination of the plaquing efficiency of the isolates was performed as previously described. One isolate was selected for further study and designated C. muridarum CM3.1. CM3.1 lacked the 7.5 kb cryptic plasmid and was unable to accumulate glycogen within its inclusions. In all other respects CM3.1 resembled the parental CM972 strain. The basis of the mutation that permits restoration of the normal plaquing efficiency and plaque size is currently unknown.

Example 3

Figure 9:
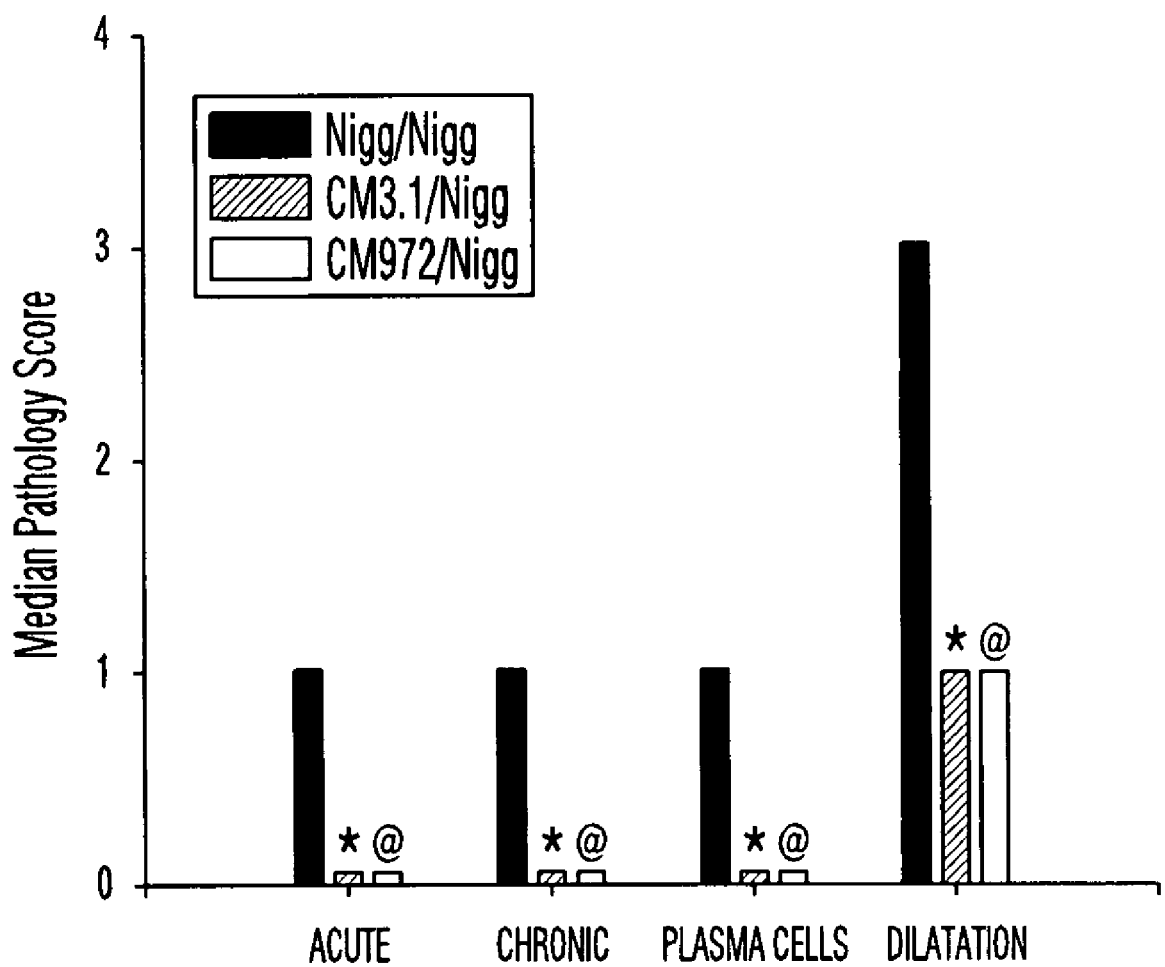
FIG. 9. The oviducts of mice primarily infected with plasmid-deficient *C. muridarum* and challenged with Nigg exhibit minimal pathology compared to mice primarily infected and challenged with Nigg.

Assessment of In Vivo Growth C. muridarum Strains CM972 and CM3.1 and Host Response to Infection In Vivo and In Vitro C. muridarum CM972 induces an in vivo infection of reduced intensity in the mouse model of ascending genital infection while in vivo infection with strain CM3.1 resembles the wild type strain *C. muridarum* Nigg. To test the efficiency with which *C. muridarum* CM972 and CM3.1 infect genital tract cells in vivo, groups of five progesterone-treated female mice of the C3H/HeN strain were inoculated intravaginally with $3\times10^5$ IFU of wild-type *C. muridarum* Nigg, CM972 or CM3.1 delivered in 30 μl of SPG. Infection was administered with the mice under sodium pentobarbital anesthesia and the infection of individual mice was monitored by swabbing the vaginal vault and cervix at various times following infection and by enumerating IFU recovered by isolation on McCoy cell monolayers. FIG. 5 reveals the mean±SD $Log_{10}$ IFU $ml^{-1}$ of mice that tested positive for infection on that day. On average, a decrease of 1.1±0.5 $Log_{10}$ IFU $ml^{-1}$ was detected from C3H mice infected with CM972 when compared to wild-type Nigg, while no such difference was observed for strain CM3.1. When the courses of infection in mice inoculated with Nigg were compared to those of mice infected with CM972 by two-way repeated measures ANOVA, a statistical difference was found, P=0.017. The rate of resolution, however, was not determined to be statistically significantly different, P=0.164 by Rank Sum.

Neither strain *C. muridarum* CM972 nor CM3.1 cause immunpathology in the upper reproductive tract of C3H mice. Upon completion of the above experiment (day 42 post infection) the mice were killed and the reproductive tracts dissected and examined for evidence of immune damage. While 80% of the mice that had been infected with strain Nigg showed evidence of severe immunpathology, e.g. hydrosalpinx, no such pathology was observed in the reproductive tracts of mice infected with CM972, and only minimal pathology in mice infected with strain CM3.1 (Table 4). These observations were subsequently confirmed via histopathology.

TABLE 4

| Strain | Number with Oviduct Pathology | P value, (z-test for sample proportions) |
|---|---|---|
| Nigg | 8/10 (4/10 with hydrosalpinx 4/10 with marked swelling) | |
| CM972 | 0/10 | 0.001 |
| CM3.1 | 2/12 (mild swelling) | 0.012 |

Human endocervical epithelial cells infected with strains CM972 or CM3.1 make less IL-8 than cells infected with the wild type strain Nigg. Transformed human endocervical cells were infected via centrifugation with the Chlamydial strains at several different multiplicities of infection. Culture supernatants from the cells were harvested at 24 and 48 hours post infection and assayed for the presence of the inflammatory cytokine IL-8. Both CM972- and CM3.1-infected cells made significantly less IL-8 when compared to cells infected with strain Nigg at both time points examined (FIGS. 6 and 7).

Conclusions. The data of this Example show that *C. muridarum* CM3.1 infects mice in vivo with approximately the same efficiency as wild-type *C. muridarum* strain Nigg. But *C. muridarum* CM3.1 induces less inflammation and pathology in vivo and induces less secretion of the pro-inflammatory cytokine IL-8 in vitro than strain Nigg. In contrast, strain CM972, infects mice in vivo with a lower efficiency than strains Nigg and CM3.1. This is consistent with strain CM972's reduced infection efficiency in vitro without the assistance of centrifugation.

The recoverable plaque forming units of both strain Nigg and strain CM3.1 declined over the course of the infection in mice. This indicates the immune system of the mouse was clearing the animal of the infection. This indicates that both strain Nigg and strain CM3.1 induced a protective immune response, even though strain CM3.1 caused almost no pathology. Thus, strain CM3.1 is likely to be an effective vaccine strain.

Example 4

Prior Infection with Plasmid-Deficient *C. muridarum* does not Prevent Reinfection with Strain Nigg but Protects Against Development of Chlamydial Disease After Challenge with Strain Nigg Prior infection with plasmid-deficient *C. muridarum* does not protect against re-infection with strain Nigg. A single experiment was conducted in which groups containing five progesterone-treated C3H mice were each inoculated intravaginally with $3\times10^5$ IFU $ml^{-1}$ of *C. muridarum* strains Nigg, CM3.1, or CM972. The intensity and duration of infection was determined by quantitative culture of cervicovaginal swabs taken at intervals through day 45 (FIG. 8) at which time all mice were no longer infected. The courses of infection were similar between the groups, as had been determined previously (FIG. 5). Each group of mice was then inoculated with $3\times10^5$ IFU $ml^{-1}$ of *C. muridarum* strain Nigg 54 days post noted resolution of primary infection (98 days post primary infection), and the intensity and duration of the challenge infection was determined as above. Prior genital tract infection with a homologous strain did not protect against re-infection and this was observed for the mice primarily infected and subsequently challenged with *C. muridarum* Nigg (5/5, FIG. 9). Nevertheless, the intensity and duration of challenge infection in the lower genital tract was reduced in mice that had been primarily infected with Nigg, (P<0.001 for primary vs. challenge infection by two-way RM ANOVA). The course of Nigg challenge infection in mice primarily infected with CM972 was reduced compared to primary CM972 infection, although the difference did not reach statistical significance, (P=0.05). Only 4 of 5 mice primarily infected with CM972 became infected with Nigg upon challenge (FIG. 9). Mice primarily infected with CM3.1 and challenged with Nigg also sustained a reduced infection (5/5, FIG. 9), but again the difference between primary and challenge infections was not statistically significant, (P=0.18). Clearance of lower tract infection with Nigg by mice infected with either CM972 or CM3.1 was clearly delayed (FIG. 9).

Prior infection with plasmid-deficient *C. muridarum* protects against the development of Chlamydial disease after challenge with strain Nigg. The mice were sacrificed 42 days after challenge (140 days from primary infection) and genital tract tissues were harvested and examined for histopathology (Darville et al., 1997). Oviduct inflammatory parameters were statistically significantly higher in mice primarily infected, then subsequently challenged with Nigg when compared with mice that had been primarily infected with either CM972 or CM3.1 (FIG. 9). Eight of 10 oviducts from mice primarily infected with Nigg and subsequently challenged with Nigg exhibited hydrosalpinx, compared to 2 of 10 oviducts from mice primarily infected with CM3.1. In mice primarily infected with CM972, hydrosalpinx was not seen. Furthermore, 6/10 oviducts from Nigg/Nigg infected mice showed evidence of scarring fibrosis, a pathological finding not observed for the mice primarily infected with the plasmid-deficient strains and challenged with Nigg.

Thus, the mice primarily infected with the plasmid-deficient strains were protected against the development of chlamydial disease when challenged with a fully virulent strain, even when the clearance of the virulent strains appears somewhat delayed.

TLR2 colocalizes with the inclusions of cells infected with *C. muridarum* and with the plasmid-deficient strain CM3.1. We have previously demonstrated the recruitment of toll-like receptor-2 (TLR2) and the signaling adaptor MyD88 to the inclusion membrane of *C. trachomatis-infected* epithelial cells, suggesting that TLR2 was actively engaged in signaling from this intracellular niche (O'Connell et al., 2006). Since the plasmid-deficient mutants are defective in inducing production of IL-8, a TLR2-dependent response, the possibility that this is a consequence of aberrant trafficking of TLR2 to the chlamydial inclusion membrane needed to be evaluated. HEK293 cells expressing CFP-conjugated TLR2 (green) were infected with either *C. muridarum* Nigg or with the plasmid-deficient strains CM3.1. Cells were fixed 24 hours p.i. and stained with an anti-chlamydial LPS monoclonal (red) before being examined by confocal microscopy. Confocal microscopy revealed that CFP-TLR2 clearly co-localized with the chlamydial inclusions formed by both *C. muridarum* Nigg and strain CM3.1 demonstrating that trafficking of the TLR2 receptor to the inclusion membrane had not been perturbed in cells infected with plasmid-deficient chlamydiae (data not shown).

This observation indicates that the deficiency in TLR2-dependent signaling that we have observed during genital tract infection by plasmid-deficient chlamydiae is not due to an intracellular trafficking failure that prevents recruitment of the receptor to the inclusion.

Example 5

Plasmid-Deficient Strains of *C. muridarum* do not Stimulate Toll-Like Receptor 2-Dependent Signaling Materials and Methods:

Murine infection and analysis. Six- to 8-week-old female C3H/HeouJ mice were obtained from The Jackson Laboratory, and mice homozygous for $Tlr2^{tm1Aki}$ were generously provided by Shizuo Akira (Osaka, Japan). Mice were injected intravaginally as described (30) with 30 μl of SPG containing $3 \times 10^5$ IFU of *C. muridarum* Nigg, CM972, or CM3.1. Mice were monitored for cervicovaginal shedding as described (Darville et al., 2003). Bacterial burden in oviduct tissues was measured by PFU determination on McCoy cells as in Example 1. Oviducts dissected free from the uterine horns of a single mouse were homogenized in 1 ml of protease inhibitor buffer and an aliquot was removed for isolation and titration of chlamydiae. All animal experiments were pre-approved by the University of Arkansas for Medical Sciences Institutional Animal Care and Use Committee.

Genital tract secretions were collected and analyzed for cytokines as described previously (Darville et al. 2003). Histopathological analysis of fixed genital tract tissues was performed as described (Darville et al., 1997). Sera from mice were collected by retroorbital bleeds at the time of sacrifice and stored at −20° C. until analyzed by ELISA as previously described (Darville et al., 1997). Preimmune sera were used as negative controls. The titer for individual mice was determined as the highest serum dilution with an optical density value greater than that of the control wells.

In vitro analysis of cellular responses. The following cell lines were examined: human embryonic kidney (HEK) 293 cells stably expressing TLR2 and MyD88 (Latz et al. 2002), a human papillomavirus 16/E6E7 immortalized ectocervical epithelial cell line (ShEC) (Komisarova et al., 1994). In addition, in vitro infection was performed in murine BMDDCs grown from bone marrow cultures following the procedure of Inaba et al. (Inaba et al., 1992). The TLR2 agonist, $Pam_3Cys$-$Ser$-$(Lys)_4$ (Axxora, LLC, San Diego, Calif.) or recombinant human TNF-α (R&D Systems, Minneapolis, Minn.) were used as positive control stimulants. Cells were plated in 24-well tissue culture dishes at a density of $10^5$ cells per well. Infections were carried out by overlaying cells with a multiplicity of 0.5-5. Cells were incubated for 18-40 h at 37° C., 5% $CO_2$. Supernatant was harvested and assayed for IL-8 using a DuoSet ELISA kit from R&D Systems, or for IL-1β, IL-2, IL-4, IL-5, IL-6, IL-10, IL-12p40/p70, GM-CSF, IFN-γ and TNF-α by multiplex bead cytokine arrays (Biosource, Camarillo, Calif.). All data points were assayed in triplicate and reported as the mean±S.D.

Statistics. The ANOVA plus post hoc test was used to analyze differences in cytokine production among various in vitro groups. Statistical comparisons between the murine strains for level of infection and cytokine production over the course of infection were made by a two-factor (days and murine strain) analysis of variance with post hoc Holm-Sidak test as a multiple comparison procedure. The Wilcoxon rank sum test was used to compare the duration of infection in the respective strains over time. The Kruskal Wallis one-way ANOVA on ranks was used to determine significant differences in the pathological data between groups. The z-test for determination of significant differences in sample proportions was used to compare frequencies of pathological findings between specific groups. SigmaStat software was utilized (SPSS Science, Chicago, Ill.)

Figure 10:
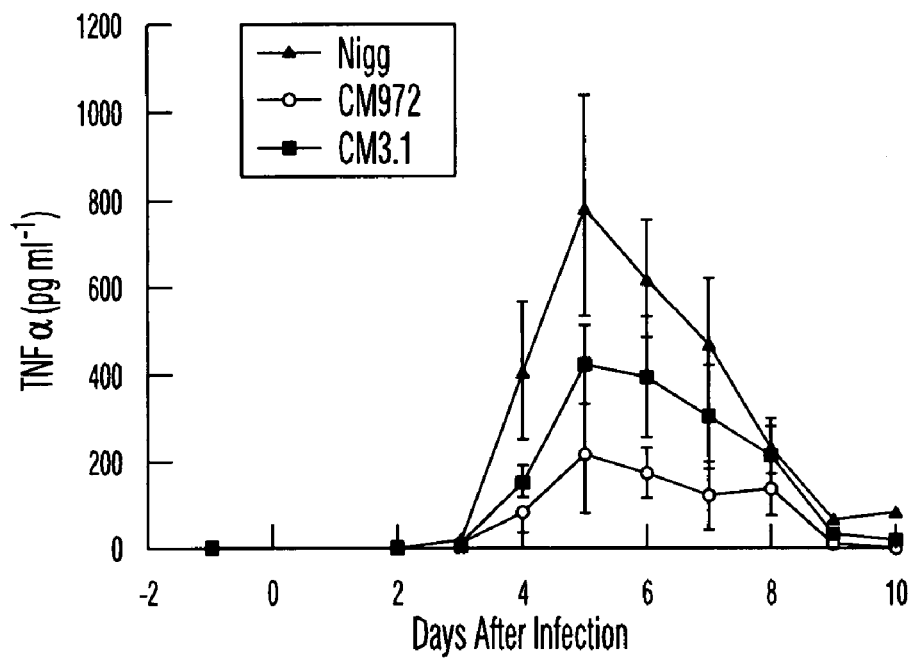
FIG. 10 is a bar chart of pathology scores of oviducts from mice primarily infected with strains Nigg, CM3.1, or CM972 and subsequently challenged with Nigg. Acute, chronic, plasma cell infiltrates, and oviduct dilatation were significantly decreased in mice primarily infected with CM3.1 or CM972, and challenged on day 98 p.i. with Nigg vs. mice primarily infected with Nigg and challenged with Nigg. Each bar=median pathology score calculated from 10 oviducts from 5 mice sacrificed 42 d post-challenge infection; Nigg=black bars; CM972=white bars; CM3.1=gray bars. *:$P<0.001$ for 3.1/Nigg vs Nigg/Nigg, @: $P<0.001$ for 972/Nigg vs. Nigg/Nigg (ANOVA on Ranks).

Results:

The absence of oviduct pathology in mice infected with plasmid-deficient *C. muridarum* is caused by a failure to activate signal transduction via TLR2. Our prior studies have established an essential role for TLR2 in the induction of oviduct pathology associated with *C. muridarum* infection (Darville et al., 2003). While TLR2KO mice experienced an unaltered infection course, they exhibited a marked reduction in chronic oviduct pathology compared to WT mice. To investigate the possible mechanism of this reduced pathology, we compared TNF-α and MIP-2 levels in genital tract secretions of mice infected with the plasmid-deficient strains to those from mice infected with Nigg during the first 10 days of infection. Significantly reduced levels of TNF-α (FIG. 10) and macrophage inflammatory protein-2 (MIP-2, not shown)

were observed; resembling the decreased responses described in Nigg-infected TLR2KO mice (Darville et al., 2003).

Figure 11:
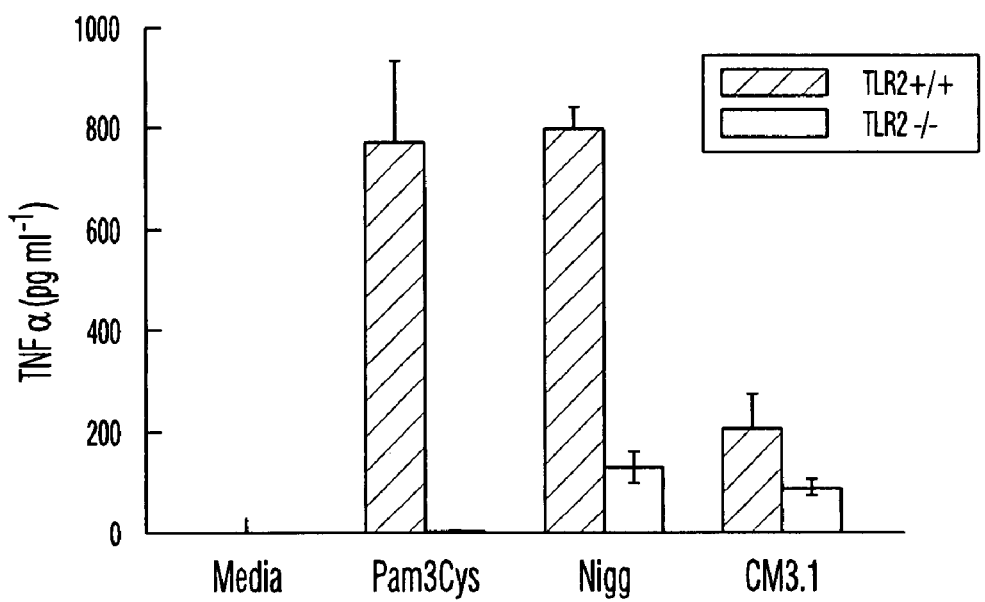
FIG. 11. Plasmid-deficient strains induce TNF-α responses in wild type DCs similar to those induced by Nigg in TLR2KO DCs. Supernatants from wild type DCs (hatched bars) or TLR2KO DCs (white bars) cultured 24 h with MOI=2 of Nigg or CM3.1, or the positive control TLR2-ligand, Pam3Cys were assayed for TNF-α by bead array. Bars=means±SD calculated from triplicate wells in a single representative experiment.

Purified and rested bone marrow-derived dendritic cells (BMDDCs) were incubated with chlamydiae at an MOI of 1 or 2 as described previously for macrophages (Darville et al., 2003). After 24 hours, an aliquot of supernatant was harvested and assayed for cytokines. Intracellular staining of the infected dendritic cells (DCs) with anti-chlamydial LPS antibody 3 and 24 hours post-infection revealed that all three strains of C. muridarum had been taken up and eliminated by 24 hours. No inclusions were observed, consistent with the report of Zhang et al. (1999) that C. muridarum does not replicate in DCs. Dendritic cell supernatants were analyzed for IL-1β, IL-2, IL-4, IL-5, IL-6, IL-10, IL-12p40/p70, granulocyte-macrophage colony-stimulating factor (GM-CSF), IFN-γ and TNF-α. Of the cytokines assayed, incubation of the DCs with Nigg led to significant increases above media controls for IL-6, IL-12p40/p70, TNF-α, and GM-CSF. Dendritic cells incubated with CM3.1 (FIG. 11) or CM972 (data not shown) secreted these cytokines at significantly reduced levels. Furthermore, the cytokine responses elicited by the plasmid-deficient strains were similar to those induced by Nigg in TLR2 knock-out DCs (TLR2KO DCs) (FIG. 11).

Figure 12A:
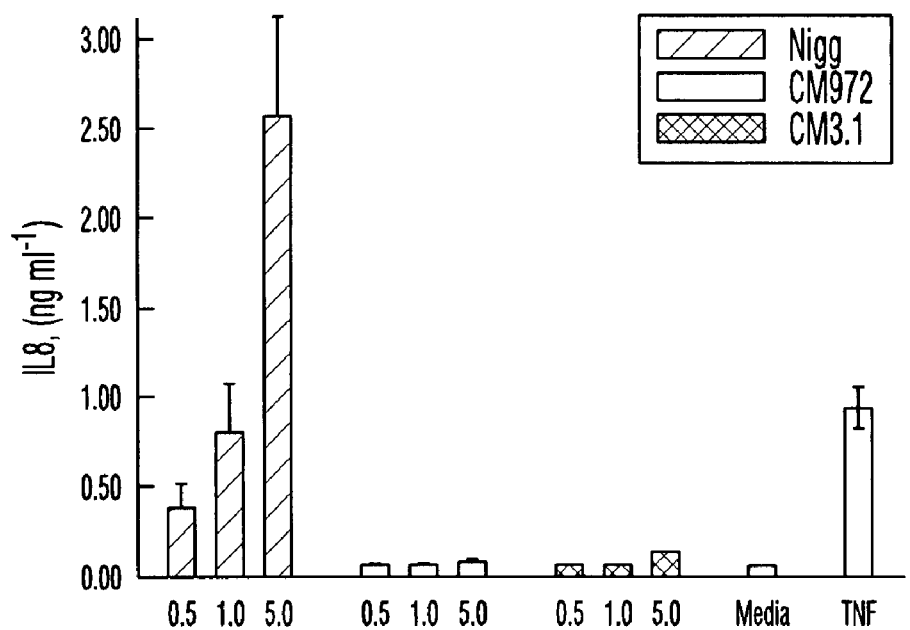
FIGS. 12A and 12B. Plasmid-deficient strains of *C. muridarum* fail to induce TLR2-dependent secretion of IL-8 in (A) human cervical epithelial cells or (B) HEK293/TLR2 cells. Supernatants 24 h post infection with Nigg, CM972, or CM3.1 at MOIs of 0.5, 1, and 5 were assayed by ELISA for IL-8. Bars=means±SD IL-8 concentration calculated from triplicate wells.
Figure 12B:
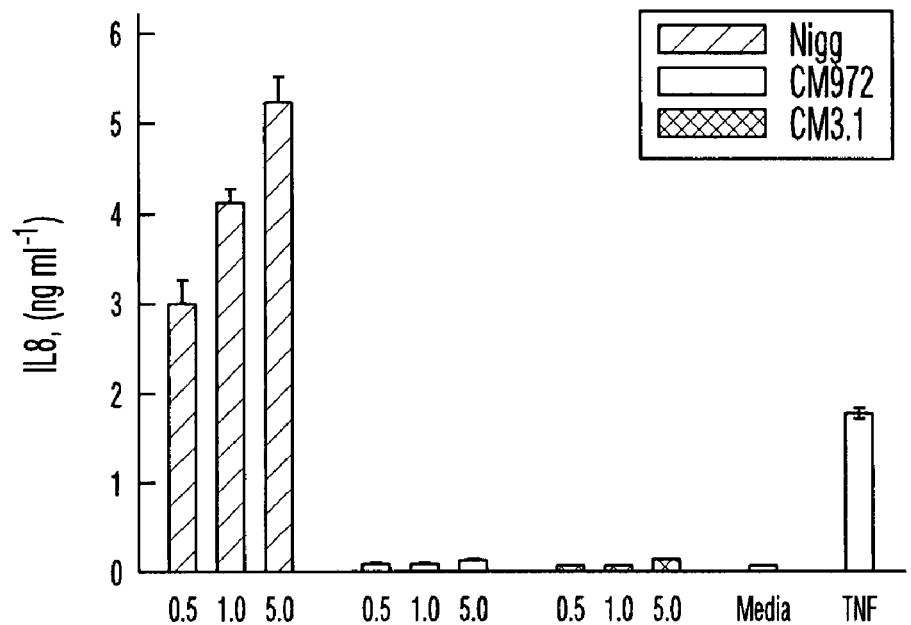

Cervical epithelial cells play a critical role in early immune signaling in response to infection by sexually transmitted pathogens. It has been previously reported that primary and immortalized human cervical epithelial cells express a variety of TLRs, with the exception of TLR4 and the associated protein MD-2 (Fichirova et al. 2002). In subsequent studies, we showed that infection of immortalized human ectocervical epithelial cells (ShEC) with C. trachomatis resulted in a dose-dependent induction of IL-8 secretion that was entirely dependent on MyD88 expression (O'Connell et al., 2006). Using HEK293 cells stably transfected with TLR2, or TLR4/MD-2, we determined that Chlamydia-induced IL-8 secretion was predominantly TLR2-dependent, with minimal TLR4-dependent activity (O'Connell et al., 2006). To investigate the effect of infection by C. muridarum Nigg and its plasmid-deficient derivatives on the secretion of IL-8 by relevant epithelial cells, ShEC and HEK 293/TLR2 cells were infected in triplicate. After 24 h incubation, the culture supernatants were analyzed for the presence of IL-8 by ELISA. In both the ShEC cells (FIG. 12A) and HEK293/TLR2 cells (FIG. 12B) a dose-dependent increase in IL-8 secretion occurred in response to infection with Nigg. However, infection with CM972 or CM3.1 did not result in any increase in IL-8 secretion over that seen with cells cultured in media alone (FIGS. 12A and 12B). The infectious progeny from these cell cultures were enumerated on McCoy cells, and no differences were observed between the strains (data not shown). Thus, although the plasmid-deficient strains productively infect human epithelial cells at a level equivalent to Nigg, active replication of the attenuated strains failed to elicit TLR2-dependent cell activation.

Figure 8A:
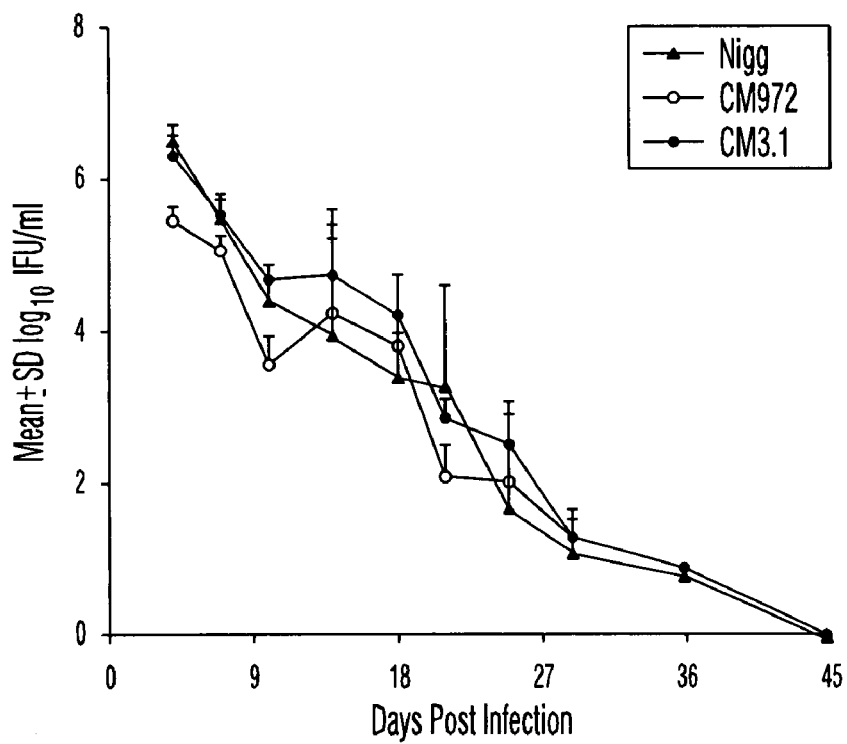
FIG. 8. Course and duration of lower genital tract infection in mice challenged with *C. muridarum* Nigg after resolution of a primary infection with either strain Nigg, or the plasmid-deficient strains CM972 and CM3.1.
Figure 8B:
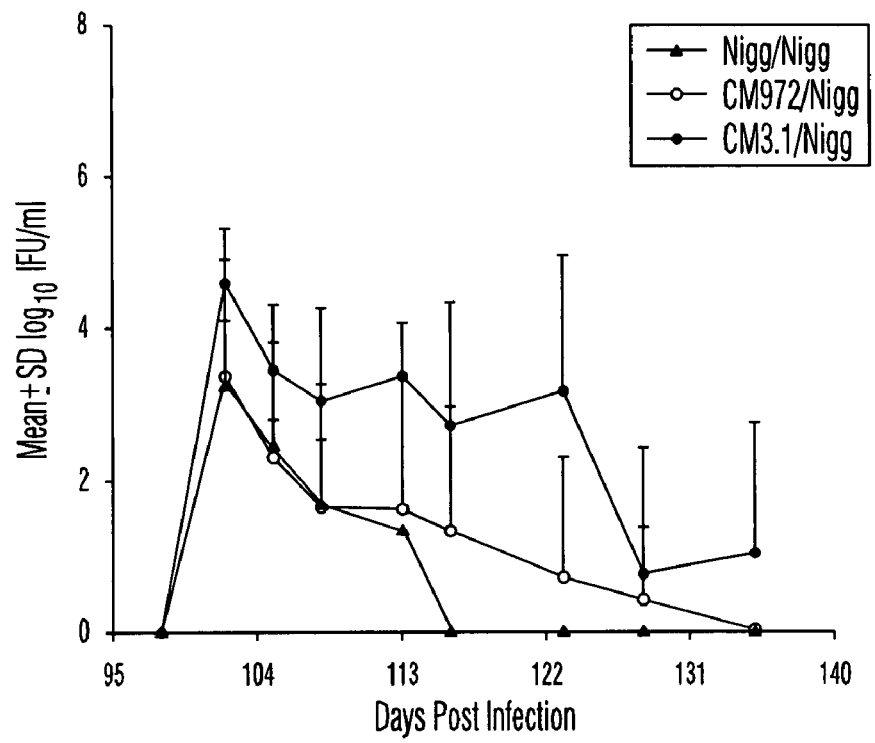

Infection of mice with either CM972 or CM3.1 results in Th1-predominant adaptive immune responses as seen in mice infected with the parental Nigg strain. Multiple studies of murine chlamydial infection report a preponderance of IgG2a vs. IgG1, reflective of a Th1-dominant response. Using ELISA (Darville et al., 1997) we detected C. muridarum EB-specific IgG2a in serum taken from mice infected with Nigg, CM972, or CM3.1 on day 28 post infection. Titers of IgG2a were not different among the groups (mean±SD $\log_{10}$ IgG2a=3.3±0.2 for Nigg, 2.8±0.4 for CM972, and 3.2±0.4 for CM3.1). IgG1 was low or absent. We also evaluated the chlamydia-specific T cell proliferative response in the draining iliac nodes of mice 28 days post infection. The Iliac node cells from mice infected with Nigg or the plasmid-deficient strains exhibited robust $CD4^+$ T cell responses after stimulation in vitro with UV-inactivated EBs (data not shown). The equivalent rate of resolution of lower genital tract infection (FIG. 8a), the detection of normal titers of IgG2a antibodies, and the detection of normal T cell responses indicated an intact adaptive response in mice infected with plasmid-deficient strains in the absence of TLR2-dependent signaling.

Discussion:

These Examples describe a pair of C. muridarum mutants that are attenuated in their ability to cause disease but retain the ability to infect their murine host. The plasmid-deficient strain CM972 has an attachment/uptake defect in cell culture (Example 1). This observation may explain why plasmid-deficient strains are so rarely observed amongst clinical isolates of *C. trachomatis*. Spontaneous loss of the plasmid during infection may lead to a competitive disadvantage and ultimately reduced transmissibility. However, the attachment and uptake defect associated with CM972 was not responsible for the failure of this strain to induce oviduct pathology because strain CM3.1, a spontaneous mutant derived from CM972, does not induce oviduct pathology while it infects normally in cell culture and in vivo. Thus, loss of the plasmid from *C. trachomatis* is pleiotropic, impacting two virulence-associated phenotypes in addition to the ability of the chlamydiae to accumulate glycogen within their inclusion.

This Example suggests that the inability of CM972 and CM3.1 to cause pathology is at least partly because neither strain is capable of stimulating a TLR2-dependent response. Previous work has associated TLR2-dependent cytokine production with the induction of oviduct pathology by chlamydiae (Darville et al., 2003). Evaluation of the ability of the plasmid-deficient strains to elicit TLR2-dependent cytokines during in vivo infection revealed a deficiency in the extent of their response. The signaling defect was consistently observed in sentinel cells such as dendritic cells and cervical epithelium, and was confirmed in reconstituted TLR2-expressing epithelial cells. The possibility that the plasmid-deficient strains were limited in their ability to infect oviduct epithelium was ruled out as a contributor to reduced pathology because inclusions could be observed via immunohistochemical staining and infectious bacteria were recovered from dissected oviducts of infected mice.

Despite failure to elicit TLR2-dependent signaling, the plasmid-deficient strains induced a normal adaptive immune response that protected against pathology upon challenge with the wild-type strain. This observation suggests that a functional Th1 adaptive immune response does not contribute to the development of oviduct pathology via collateral damage, as has been hypothesized by others (Brunham et al. 2005). Furthermore, an adaptive Th1 response that limits the infectious burden may be sufficient to protect against deleterious TLR2-induced innate responses that are inevitable upon challenge with wild-type chlamydiae. Thus, the induction of sterilizing immunity may not be necessary for an effective vaccine against chlamydial genital tract disease. Recent studies using candidate chlamydial antigens paired with Th1-inducing adjuvants (Pal et al., 2006; Murthy et al., 2007) support this conclusion.

CITED REFERENCES

Banks, J., Eddie, B., Schachter J & Meyer, K. F. (1970). Plaque formation by *Chlamydia* in L cells. *Infect Immun* 1, 259-262.

Brunham, R. C. & Rey-Ladino, J. (2005) *Nat. Rev. Immunol* 5, 149-161.

Chin, S. C., Abdullah, N. Siang, T. W. & Wan, H. Y. (2005). Plasmid profiling and curing of *Lactobacillus* strains isolated from the gastrointestinal tract of chicken. *J. Microbiol.* 43, 251-256.

Comanducci, M., Cevenini, R., Moroni, A., Giuliani, M. M., Ricci, S., Scarlato, V. & Ratti, G. (1993). Expression of a plasmid gene of *Chlamydia trachomatis* encoding a novel 28 kDa antigen. *J Gen Microbiol* 139 (Pt 5), 1083-1092.

Danesh J, Collins R, Peto R. (1997). Chronic infections and coronary heart disease: is there a link? *Lancet.* 350(9075), 430-6.

Darville, T., Andrews, C. W., Jr., Laffoon, K. K., Shymasani, W., Kishen, L. R. & Rank, R. G. (1997) *Infect. Immun.* 65, 3065-3073.

Darville T, O'Neill J M, Andrews C W Jr, Nagarajan U M, Stahl L, Ojcius D M. (2003). Toll-like receptor-2, but not Toll-like receptor-4, is essential for development of oviduct pathology in Chlamydial genital tract infection. *J Immunol.* 171(11), 6187-97.

Dean, D., Oudens, E., Bolan, G., Padian, N. & Schachter, J. (1995). Major outer membrane protein variants of *Chlamydia trachomatis* are associated with severe upper genital tract infections and histopathology in San Francisco. *J Infect Dis* 172, 1013-1022.

Farencena, A., Comanducci, M., Donati, M., Ratti, G. & Cevenini, R. (1997). Characterization of a new isolate of *Chlamydia trachomatis* which lacks the common plasmid and has properties of biovar trachoma. *Infect Immun* 65, 2965-2969.

Fichorova, R. N., Cronin, A. O., Lien, E., Anderson, D. J. & Ingalls, R. R. (2002) *J. Immunol.* 168, 2424-2432.

Fong I W, Chiu B, Viira E, Fong M W, Jang D, Mahony J. (1997). Rabbit model for *Chlamydia pneumoniae* infection. *J Clin Microbiol.* 35(1), 48-52.

Gado, I., Toth, I. & Szvoboda, G. (1987). Curing of plasmid pE194 with novobiocin and coumermycin A1 in *Bacillus subtilis* and *Staphylococcus aureus. Zentralbl Bakteriol Mikrobiol Hyg [A]* 265, 136-145.

Gerbase A C, Rowley J T, Mertens T E. (1998) Global epidemiology of sexually transmitted diseases. *Lancet.* 351 Suppl 3, 2-4.

Grayston J T, Wang S P, Kuo C C, Campbell L A. (1989) Current knowledge on *Chlamydia pneumoniae*, strain TWAR, an important cause of pneumonia and other acute respiratory diseases. *Eur J Clin Microbiol Infect Dis.* 8(3), 191-202.

Grayston J T, Aldous M B, Easton A, Wang S P, Kuo C C, Campbell L A, Altman J. (1993). Evidence that *Chlamydia pneumoniae* causes pneumonia and bronchitis. *J Infect Dis.* 168(5), 1231-5.

Hooper, D. C., Wolfson, J. S., McHugh, G. L., Swartz, M. D., Tung, C. & Swartz, M. N. (1984). Elimination of plasmid pMG110 from *Escherichia coli* by novobiocin and other inhibitors of DNA gyrase. *Antimicrob Agents Chemother* 25, 586-590.

Inaba, K., Inaba, M., Romani, N., Aya, H., Deguchi, M., Ikehara, S., Muramatsu, S. & Steinman, R. M. (1992) *J Exp. Med* 176, 1693-1702.

Kalman, S., Mitchell, W., Marathe, R. & other authors (1999). Comparative genomes of *Chlamydia pneumoniae* and *C. trachomatis. Nat Genet* 21, 385-389.

Kelly, K. A., Robinson, E. A., & Rank, R. G. (1996). Initial route of antigen administration alters the T-cell cytokine profile produced in response to the mouse pneumonitis biovar of *Chlamydia trachomatis* following genital infection. *Infect Immun* 64:4976-83.

Komissarova E V, Pantin V I, Pavlova L S, Borovkova T V, Soifer M V, Shtutman M S, Zarytova V F, Ivanova E M, Sats N V, Grineva N I, et al. (1994). Expression of transcription of human papillomavirus type 18 (HPV 18) E6 and E7 genes in transformed rat fibroblasts: use of an antisense oligonucleotide to the E7 gene. *Dokl Akad Nauk.* 338(3): 404-7.

Laitinen K, Laurila A, Pyhala L, Leinonen M, Saikku P. (1997). *Chlamydia pneumoniae* infection induces inflammatory changes in the aortas of rabbits. *Infect Immun.* 65(11), 4832-5.

Lee, C. K. (1981). Interaction between a trachoma strain of *Chlamydia trachomatis* and mouse fibroblasts (McCoy cells) in the absence of centrifugation. *Infect Immun* 31, 584-591.

Lusher, M., Storey, C. C. & Richmond, S. J. (1989). Plasmid diversity within the genus *Chlamydia. J Gen Microbiol* 135 (Pt 5), 1145-1151.

Luttinger, A. (1995). The twisted 'life' of DNA in the cell: bacterial topoisomerases. *Mol Microbiol* 15, 601-606.

Matsumoto, A., Izutsu, H., Miyashita, N. & Ohuchi, M. (1998). Plaque formation by and plaque cloning of *Chlamydia trachomatis* biovar trachoma. *J Clin Microbiol* 36, 3013-3019.

McClenaghan, M., Honeycombe, J. R., Bevan, B. J. & Herring, A. J. (1988). Distribution of plasmid sequences in avian and mammalian strains of *Chlamydia psittaci. J Gen Microbiol* 134 (Pt 3), 559-565.

Miyashita, N., Matsumoto, A. & Matsushima, T. (2000). In vitro susceptibility of 7.5-kb common plasmid-free *Chlamydia trachomatis* strains. *Microbiol. Immunol* 44, 267-269.

Murthy, A. K., Chambers, J. P., Meier, P. A., Zhong, G., & Arulanandam, B. P. (2007) *Infect. Immun.* 75, 666-676.

Nigg, C. (1942). An unidentified virus which produces pneumonia and systemic infection in mice. *Science* 95, 49-50.

O'Connell, C. M., Ionova, I. A., Quayle, A. J., Visintin, A. & Ingalls, R. R. (2006) *J. Biol. Chem.* 281, 1652-1659.

Pal, S., Peterson, E. M., Rappuoli, R., Ratti, G., & De La Maza, L. M. (2006) *Vaccine* 24, 766-775.

Pearce, J. H., Allan, I. & Ainsworth, S. (1981). Interaction of Chlamydiae with host cells and mucous surfaces. *Ciba Found Symp* 80, 234-249.

Perez-Martinez J A, Storz J. (1985). Antigenic diversity of *Chlamydia psittaci* of mammalian origin determined by microimmunofluorescence. *Infect Immun.* 50(3), 905-10.

Peterson, E. M., Markoff, B. A., Schachter, J. & De La Maza, L. M. (1990). The 7.5-kb plasmid present in *Chlamydia trachomatis* is not essential for the growth of this microorganism. *Plasmid* 23, 144-148.

Pickett, M. A., Everson, J. S., Pead, P. J. & Clarke, I. N. (2005). The plasmids of *Chlamydia trachomatis* and *Chlamydophila pneumoniae* (N16): accurate determination of copy number and the paradoxical effect of plasmid-curing agents. *Microbiology* 151, 893-903.

Pinto L A, Edwards J, Castle P E, Harro C D, Lowy D R, Schiller J T, Wallace D, Kopp W, Adelsberger J W, Baseler M W, Berzofsky J A, Hildesheim A. (2003). Cellular immune responses to human papillomavirus (HPV)-16 L1 in healthy volunteers immunized with recombinant HPV-16 L1 virus-like particles. *J Infect Dis.* 188(2), 327-38.

Read, T. D., Brunham, R. C., Shen, C. & other authors (2000). Genome sequences of *Chlamydia trachomatis* MoPn and *Chlamydia pneumoniae* AR39. *Nucleic Acids Res* 28, 1397-1406.

Read, T. D., Myers, G. S., Brunham, R. C. & other authors (2003). Genome sequence of *Chlamydophila caviae* (*Chlamydia psittaci* GPIC): examining the role of niche-specific genes in the evolution of the Chlamydiaceae. *Nucleic Acids Res* 31, 2134-2147.

Rota, T. R. (1977). *Chlamydia trachomatis* in cell culture. II. Susceptibility of seven established mammalian cell types in vitro. Adaptation of trachoma organisms to McCoy and BHK-21 cells. *In Vitro* 13, 280-292.

Sabet S F, Simmons J, Caldwell H D. (1984). Enhancement of *Chlamydia trachomatis* infectious progeny by cultivation of HeLa 229 cells treated with DEAE-dextran and cycloheximide. *J. Clin Microbiol* 20(2), 217-222.

Schachter J & Dawson, C. R. (1978). Laboratory Diagnosis. In *Human Chlamydial Infections*, pp. 181-220: PSG Publishing Company Inc.

Stephens, R. S., Kalman, S., Lammel, C. & other authors (1998). Genome sequence of an obligate intracellular pathogen of humans: *Chlamydia trachomatis*. *Science* 282, 754-759.

Storz, J. (1988). Overview of animal diseases induced by Chlamydial infections, p. 167-192 In A L Barron (ed.), *Microbiology of Chlamydia*. CRC Press, Inc., Boca Raton, Fla.

Stothard, D. R., Williams, J. A., Van Der, P. B. & Jones, R. B. (1998). Identification of a *Chlamydia trachomatis* serovar E urogenital isolate which lacks the cryptic plasmid. *Infect Immun* 66, 6010-6013.

Tam, J. E., Davis, C. H., Thresher, R. J. & Wyrick, P. B. (1992). Location of the origin of replication for the 7.5-kb *Chlamydia trachomatis* plasmid. *Plasmid* 27, 231-236.

Thomas, N. S., Lusher, M., Storey, C. C. & Clarke, I. N. (1997). Plasmid diversity in *Chlamydia*. *Microbiology* 143 (Pt 6), 1847-1854.

Tropp, B. E., Ragolia, L., Xia, W., Dowhan, W., Milkman, R., Rudd, K. E., Ivanisevic, R. & Savic, D. J. (1995). Identity of the *Escherichia coli* cls and nov genes. *J Bacteriol* 177, 5155-5157.

Wolfson, J. S., Hooper, D. C., Swartz, M. N., Swartz, M. D. & McHugh, G. L. (1983). Novobiocin-induced elimination of F'lac and mini-F plasmids from *Escherichia coli*. *J Bacteriol* 156, 1165-1170.

Zhang, D., Yang, X., Lu, H., Zhong, G. & Brunham, R. C. (1999) *Infect. Immun.* 67, 1606-1613.

All patents, patent documents, and other references cited are hereby incorporated by reference.

---

What is claimed is:

1. An isolated plasmid-deficient *Chlamydia* sp. strain wherein the strain causes reduced pathology as compared to a corresponding plasmid-containing disease-causing *Chlamydia* strain in a vertebrate; and wherein following inoculation with the plasmid-deficient *Chlamydia* strain, when a vertebrate is infected with the corresponding plasmid-containing disease-causing strain the vertebrate experiences reduced pathology as compared to a vertebrate not previously inoculated with the plasmid-deficient *Chlamydia* strain;

wherein the strain is prepared by a process comprising:

treating the plasmid-containing disease-causing *Chlamydia* sp. strain under conditions that cure it of the plasmid to generate a population of treated *Chlamydia*;

incubating host cells with the treated *Chlamydia* under conditions permissive for infection by plasmid-deficient *Chlamydia* to infect the host cells;

culturing the *Chlamydia* in the host cells and isolating plaques of *Chlamydia* from the host cells; and verifying that *Chlamydia* from the isolated plaques are plasmid-deficient; and wherein the strain does not stimulate TLR2-dependent IL-8 secretion.

2. The isolated plasmid-deficient *Chlamydia* sp. strain of claim 1 wherein the strain is a *C. trachomatis* strain.

3. The isolated plasmid-deficient *Chlamydia* sp. strain of claim 2 wherein the step of incubating host cells with the treated *Chlamydia* under conditions permissive for infection by plasmid-deficient *Chlamydia* to infect the host cells comprises centrifuging the treated *Chlamydia* onto the host cells.

4. The isolated plasmid-deficient *Chlamydia* sp. strain of claim 1 wherein the step of incubating host cells with the treated *Chlamydia* under conditions permissive for infection by plasmid-deficient *Chlamydia* to infect the host cells comprises centrifuging the treated *Chlamydia* onto the host cells.

* * * * *

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial
<220> FEATURE:
<223> OTHER INFORMATION: Primer

<400> SEQUENCE: 1
cactacgctc acgtggactg                                              20

<210> SEQ ID NO 2
<211> LENGTH: 20
<212> TYPE: DNA
<213> ORGANISM: Artificial
<220> FEATURE:
<223> OTHER INFORMATION: Primer

<400> SEQUENCE: 2
ctctcctgca cgaccttctg                                              20

<210> SEQ ID NO 3
<211> LENGTH: 20
<212> TYPE: DNA
<213> ORGANISM: Artificial
<220> FEATURE:
<223> OTHER INFORMATION: Primer

<400> SEQUENCE: 3
tgtcacagcg gttgctctaa                                              20

<210> SEQ ID NO 4
<211> LENGTH: 20
<212> TYPE: DNA
<213> ORGANISM: Artificial
```

```
<220> FEATURE:
<223> OTHER INFORMATION: Primer

<400> SEQUENCE: 4
ctatgctgca aggaggtaag                                                          20
```